(12) United States Patent
Ferro, Jr. et al.

(10) Patent No.: US 11,610,682 B2
(45) Date of Patent: Mar. 21, 2023

(54) SYSTEMS, METHODS, AND DEVICES FOR NON-HUMAN READABLE DIAGNOSTIC TESTS

(71) Applicant: EMED LABS, LLC, Miami, FL (US)

(72) Inventors: Michael W. Ferro, Jr., Palm Beach, FL (US); Zachary Carl Nienstedt, Wilton Manors, FL (US); Sam Miller, Hollywood, FL (US); Marco Magistri, Miami, FL (US); Nicholas Atkinson Kramer, Wilton Manors, FL (US); James Thomas Heising, Richard, WA (US)

(73) Assignee: EMED LABS, LLC, Miami, FL (US)

( * ) Notice: Subject to any disclaimer, the term of this patent is extended or adjusted under 35 U.S.C. 154(b) by 0 days.

(21) Appl. No.: 17/807,934

(22) Filed: Jun. 21, 2022

(65) Prior Publication Data
US 2022/0406458 A1    Dec. 22, 2022

Related U.S. Application Data

(60) Provisional application No. 63/202,731, filed on Jun. 22, 2021, provisional application No. 63/268,663, (Continued)

(51) Int. Cl.
*G06K 9/00* (2022.01)
*A61K 35/12* (2015.01)
(Continued)

(52) U.S. Cl.
CPC ............ *G16H 50/20* (2018.01); *G16H 30/20* (2018.01); *G16H 40/67* (2018.01); *G16H 50/30* (2018.01)

(58) Field of Classification Search
CPC .................................. G06K 9/00; A61K 35/12
(Continued)

(56) References Cited

U.S. PATENT DOCUMENTS

| 7,110,525 | B1 | 9/2006 | Heller et al. |
| 7,176,936 | B2 | 2/2007 | Sauer et al. |

(Continued)

FOREIGN PATENT DOCUMENTS

| CN | 103153248 | 6/2013 |
| CN | 105266897 | 1/2016 |

(Continued)

OTHER PUBLICATIONS

Abbott, Dec. 2020, Binaxnow™ covid-19 Ag card home test and Navica™ app, https://web.archive.org/web/20201224151604/https://wwww.globalpointofcare/abbott, 3 pp.
(Continued)

*Primary Examiner* — Seyed H Azarian
(74) *Attorney, Agent, or Firm* — Knobbe Martens Olson & Bear LLP

(57) ABSTRACT

Systems and methods for ensuring medical diagnostic test integrity are disclosed. In particular, systems and methods herein can be used to ensure compliance with testing procedures. Some embodiments provide systems and methods for verifying test results. According to some embodiments, test results can be non-human-readable results that can be interpreted by a computing system.

17 Claims, 19 Drawing Sheets

Related U.S. Application Data filed on Feb. 28, 2022, provisional application No. 63/271,996, filed on Oct. 26, 2021, provisional application No. 63/264,328, filed on Nov. 19, 2021, provisional application No. 63/265,472, filed on Dec. 15, 2021, provisional application No. 63/268,407, filed on Feb. 23, 2022.

(51) Int. Cl.
　　*G16H 50/20*　　　(2018.01)
　　*G16H 40/67*　　　(2018.01)
　　*G16H 50/30*　　　(2018.01)
　　*G16H 30/20*　　　(2018.01)

(58) Field of Classification Search
USPC ........ 382/100, 103, 108, 113, 123, 128–134, 382/156, 162, 172–173, 181–196, 209, 382/219, 224, 254, 274, 276, 286–295, 382/305, 312; 600/309, 310, 322
See application file for complete search history.

(56) References Cited

U.S. PATENT DOCUMENTS

| | | | |
|---|---|---|---|
| 7,491,198 | B2 | 2/2009 | Kockro |
| 7,662,113 | B2 | 2/2010 | Pearl et al. |
| 8,108,190 | B2 | 8/2012 | Riener et al. |
| 8,253,778 | B2 | 11/2012 | Atsushi |
| 8,314,815 | B2 | 11/2012 | Navab et al. |
| 8,520,080 | B2 | 8/2013 | Havens |
| 8,485,038 | B2 | 12/2013 | Sengupta et al. |
| 8,611,988 | B2 | 12/2013 | Miyamoto |
| 8,713,130 | B2 | 7/2014 | Logan et al. |
| 8,768,022 | B2 | 8/2014 | Miga et al. |
| 8,814,691 | B2 | 12/2014 | Haddick et al. |
| 8,911,358 | B2 | 12/2014 | Koninckx |
| 8,948,935 | B1 | 3/2015 | Peeters et al. |
| 8,982,156 | B2 | 5/2015 | Maggiore |
| 9,030,446 | B2 | 7/2015 | Mistry et al. |
| 9,082,319 | B2 | 8/2015 | Shimada et al. |
| 9,111,383 | B2 | 8/2015 | Fein et al. |
| 9,256,711 | B2 | 2/2016 | Horseman |
| 9,262,743 | B2 | 3/2016 | Heins et al. |
| 9,285,871 | B2 | 5/2016 | Geisner et al. |
| 9,338,622 | B2 | 5/2016 | Bjontegard |
| 9,345,957 | B2 | 6/2016 | Geisner et al. |
| 9,380,177 | B1 | 8/2016 | Rao et al. |
| 9,424,761 | B2 | 11/2016 | Tuchschmid et al. |
| 9,498,132 | B2 | 11/2016 | Maier-Hein et al. |
| 9,547,917 | B2 | 2/2017 | Zamer |
| 9,563,266 | B2 | 3/2017 | Banerjee et al. |
| 9,600,934 | B2 | 3/2017 | Odessky et al. |
| 9,606,992 | B2 | 5/2017 | Geisner et al. |
| 9,648,436 | B2 | 10/2017 | Kraft |
| 9,788,714 | B2 | 12/2017 | Krueger |
| 9,836,888 | B2 | 12/2017 | Skidmore |
| 9,877,642 | B2 | 2/2018 | Duret |
| 9,886,458 | B2 | 2/2018 | Jung et al. |
| 9,892,561 | B2 | 2/2018 | Choukroun et al. |
| 9,898,662 | B2 | 3/2018 | Tsuda et al. |
| 9,916,002 | B2 | 5/2018 | Petrovskaya et al. |
| 9,972,137 | B2 | 7/2018 | Petrovskaya et al. |
| 10,013,896 | B2 | 8/2018 | Feins et al. |
| 10,052,026 | B1 | 10/2018 | Tran |
| 10,106,172 | B2 | 10/2018 | Wingfield et al. |
| 10,108,266 | B2 | 11/2018 | Banerjee et al. |
| 10,127,734 | B2 | 12/2018 | Stroila |
| 10,156,900 | B2 | 12/2018 | Publicover et al. |
| 10,197,803 | B2 | 2/2019 | Badiali et al. |
| 10,216,957 | B2 | 3/2019 | Jung et al. |
| 10,231,614 | B2 | 5/2019 | Krueger |
| 10,295,815 | B2 | 6/2019 | Romanowski et al. |
| 10,322,313 | B2 | 7/2019 | McKirdy |
| 10,346,889 | B1 | 8/2019 | Reiss et al. |
| 10,386,918 | B2 | 10/2019 | Shin |
| 10,430,985 | B2 | 11/2019 | Harrises et al. |
| 10,474,233 | B2 | 11/2019 | Swaminathan et al. |
| 10,524,715 | B2 | 1/2020 | Sahin |
| 10,535,202 | B2 | 1/2020 | Schmirler et al. |
| 10,540,776 | B2 | 2/2020 | Tran et al. |
| 10,559,117 | B2 | 3/2020 | Kaeser et al. |
| 10,593,092 | B2 | 5/2020 | Solomon |
| 10,643,210 | B2 | 5/2020 | Smith et al. |
| 10,660,522 | B2 | 5/2020 | Redei |
| 10,664,572 | B2 | 9/2020 | Bitran et al. |
| 10,758,209 | B2 | 9/2020 | Boctor et al. |
| 10,788,791 | B2 | 10/2020 | Gelman et al. |
| 10,802,695 | B2 | 11/2020 | Daniels et al. |
| 10,824,310 | B2 | 11/2020 | Acharya et al. |
| 10,832,488 | B2 | 12/2020 | Petrovskaya et al. |
| 10,849,688 | B2 | 12/2020 | Rios et al. |
| 10,885,530 | B2 | 1/2021 | Mercury et al. |
| 10,888,389 | B2 | 1/2021 | Draelos et al. |
| 10,892,052 | B2 | 2/2021 | Jordan et al. |
| 10,910,016 | B2 | 3/2021 | Rothschild et al. |
| 10,932,705 | B2 | 3/2021 | Muhsin et al. |
| 10,943,407 | B1 | 3/2021 | Morgan et al. |
| 10,945,807 | B2 | 3/2021 | Gibby et al. |
| 10,957,111 | B2 | 4/2021 | Weisman et al. |
| 10,984,910 | B2 | 4/2021 | Burkholz et al. |
| 10,991,190 | B1 | 4/2021 | Luthra et al. |
| 10,991,461 | B2 | 5/2021 | Divine et al. |
| 11,004,271 | B2 | 5/2021 | Cvetko et al. |
| 11,017,694 | B2 | 10/2021 | Buras et al. |
| 11,152,093 | B1 | 10/2021 | Hopen, Sr. et al. |
| 11,194,995 | B1 | 12/2021 | Profida Ferreira et al. |
| 11,219,428 | B2 | 1/2022 | Burkholz |
| 11,257,572 | B2 | 2/2022 | Narke et al. |
| 11,270,235 | B1 | 3/2022 | Daianu et al. |
| 11,289,196 | B1 | 3/2022 | Ferro, Jr. et al. |
| 11,315,053 | B1 | 4/2022 | Powell et al. |
| 11,367,530 | B1 | 6/2022 | Ferro, Jr. et al. |
| 11,440,014 | B2 * | 9/2022 | Kedia ................. C12Q 1/686 |
| 11,468,980 | B2 * | 10/2022 | Adi ........................ G16H 30/20 |
| 11,494,571 | B2 * | 11/2022 | Cooper ................. G16H 50/30 |
| 2007/0048723 | A1 | 3/2007 | Brewer et al. |
| 2009/0004055 | A1 | 1/2009 | Darrigrand et al. |
| 2009/0263775 | A1 | 10/2009 | Ullrich |
| 2010/0121156 | A1 | 5/2010 | Yoo |
| 2010/0159434 | A1 | 6/2010 | Lampotang et al. |
| 2011/0164105 | A1 | 7/2011 | Lee |
| 2011/0207108 | A1 | 8/2011 | Dorman |
| 2012/0053955 | A1 | 3/2012 | Martin et al. |
| 2012/0221960 | A1 | 8/2012 | Robinson |
| 2013/0096937 | A1 | 4/2013 | Campbell et al. |
| 2013/0253339 | A1 | 9/2013 | Reyes |
| 2013/0328997 | A1 | 12/2013 | Desai |
| 2013/0344470 | A1 | 12/2013 | Morgan et al. |
| 2014/0160264 | A1 | 6/2014 | Taylor et al. |
| 2014/0253590 | A1 | 9/2014 | Needham et al. |
| 2014/0304335 | A1 | 10/2014 | Fung et al. |
| 2015/0187048 | A1 | 7/2015 | Johnson |
| 2016/0125765 | A1 | 5/2016 | Meretei et al. |
| 2016/0189573 | A1 | 6/2016 | Bush |
| 2016/0292378 | A1 | 10/2016 | Saric |
| 2016/0371884 | A1 | 12/2016 | Benko et al. |
| 2017/0103440 | A1 | 4/2017 | Xing et al. |
| 2017/0115742 | A1 | 4/2017 | Xing et al. |
| 2017/0146801 | A1 | 5/2017 | Stempora |
| 2017/0173262 | A1 | 6/2017 | Veltz |
| 2017/0323062 | A1 | 11/2017 | Djajadiningrat et al. |
| 2018/0039737 | A1 | 2/2018 | Dempers et al. |
| 2018/0092595 | A1 | 4/2018 | Chen et al. |
| 2018/0140362 | A1 | 5/2018 | Cali et al. |
| 2018/0173913 | A1 * | 6/2018 | Pulitzer ................. G01N 33/533 |
| 2018/0197624 | A1 | 7/2018 | Robaina et al. |
| 2018/0225982 | A1 | 8/2018 | Jaeh et al. |
| 2018/0253840 | A1 | 9/2018 | Tran |
| 2018/0341919 | A1 | 11/2018 | Luhman |
| 2018/0353073 | A1 | 12/2018 | Boucher et al. |
| 2019/0000564 | A1 | 1/2019 | Navab et al. |
| 2019/0005195 | A1 | 1/2019 | Peterson |
| 2019/0012176 | A1 | 1/2019 | McHale |

(56) References Cited

U.S. PATENT DOCUMENTS

| | | |
|---|---|---|
| 2019/0020651 A1 | 1/2019 | Soon-Shiong et al. |
| 2019/0025919 A1 | 1/2019 | Tadi et al. |
| 2019/0064520 A1 | 2/2019 | Christensen |
| 2019/0073110 A1 | 3/2019 | Bradley et al. |
| 2019/0139318 A1 | 5/2019 | Tierney et al. |
| 2019/0179584 A1 | 6/2019 | Masters |
| 2019/0206134 A1 | 7/2019 | Devam et al. |
| 2019/0216452 A1 | 8/2019 | Nawana et al. |
| 2019/0259483 A1 | 8/2019 | Potts |
| 2019/0261914 A1 | 8/2019 | Davis et al. |
| 2019/0346429 A1 | 11/2019 | Harris |
| 2019/0266663 A1 | 12/2019 | Keeler et al. |
| 2019/0378080 A1 | 12/2019 | Srinivasan et al. |
| 2019/0380790 A1 | 12/2019 | Fuchs |
| 2019/0391638 A1 | 12/2019 | Khaderi et al. |
| 2020/0000401 A1 | 1/2020 | Dullen |
| 2020/0020454 A1 | 1/2020 | McGarvey |
| 2020/0020171 A1 | 3/2020 | Hendricks et al. |
| 2020/0073143 A1 | 4/2020 | MacNamara et al. |
| 2020/0101367 A1 | 5/2020 | Tran et al. |
| 2020/0152339 A1* | 5/2020 | Pulitzer ................ G16H 50/70 |
| 2020/0174756 A1 | 6/2020 | Cerar et al. |
| 2020/0175769 A1 | 7/2020 | Mandala |
| 2020/0205913 A1 | 7/2020 | Carnes et al. |
| 2020/0207501 A1 | 7/2020 | Urquhart et al. |
| 2020/0209214 A1* | 7/2020 | Zohar ................ G06F 16/5838 |
| 2020/0211291 A1 | 7/2020 | Miller et al. |
| 2020/0226758 A1 | 8/2020 | Carnes et al. |
| 2020/0250389 A1 | 9/2020 | Pulitzer et al. |
| 2020/0303044 A1 | 10/2020 | Stephen |
| 2020/0312038 A1 | 10/2020 | Samec et al. |
| 2020/0312437 A1 | 10/2020 | Wendland |
| 2020/0337631 A1 | 10/2020 | Sahin |
| 2020/0342679 A1 | 12/2020 | Soon-Shiong |
| 2020/0405257 A1 | 12/2020 | Samec et al. |
| 2020/0409159 A1 | 12/2020 | Samec et al. |
| 2021/0015583 A1 | 1/2021 | Avisar |
| 2021/0022810 A1 | 2/2021 | Mahfouz |
| 2021/0058485 A1 | 3/2021 | Devam et al. |
| 2021/0086989 A1 | 4/2021 | Luxford |
| 2021/0118029 A1 | 6/2021 | Koritala |
| 2021/0183507 A1 | 10/2021 | Shaya |
| 2021/0326474 A1 | 10/2021 | Sparks et al. |
| 2021/0327304 A1 | 11/2021 | Buras |
| 2021/0350883 A1 | 11/2021 | Li et al. |
| 2021/0358068 A1 | 11/2021 | Boszczyk et al. |
| 2022/0020236 A1 | 3/2022 | Luthra et al. |
| 2022/0074000 A1 | 3/2022 | Wong |
| 2022/0101608 A1 | 3/2022 | Hu |
| 2022/0254458 A1* | 8/2022 | Mooney ................ G06V 30/412 |

FOREIGN PATENT DOCUMENTS

| | | |
|---|---|---|
| EP | 3 872 813 | 9/2021 |
| KR | 10-2008-0012745 | 2/2008 |
| KR | 10-2018-0068703 | 6/2018 |
| WO | WO 21/044064 | 3/2021 |
| WO | WO 21/171226 | 9/2021 |

OTHER PUBLICATIONS

Baruah, Basant, "Augmented reality and QR codes—What you need to know", accessed via wayback machine for Apr. 14, 2021, beaconstac blog.

Uber expands options for prescription delivery with ScriptDrop, Mar. 24, 2021, Uber.com Blog (Year: 2021).

Zheng, Lixia, "Using Augmented Reality with Interactive Narrative to Help Paediatric Patients Take Prescription Medication", 2020, University College London.

* cited by examiner

| First \ Second | Strip 1 | Strip 2 | Strip 3 | Strip 4 | Strip 5 |
|---|---|---|---|---|---|
| Strip 1 | 0 | 0.3 | 0.4 | 0.55 | 0.5 |
| Strip 2 | 0.3 | 0 | 0.6 | 0.35 | 0.7 |
| Strip 3 | 0.4 | 0.6 | 0 | 0.4 | 0.5 |
| Strip 4 | 0.55 | 0.35 | 0.4 | 0 | 0.6 |
| Strip 5 | 0.5 | 0.7 | 0.5 | 0.6 | 0 |

FIG. 5

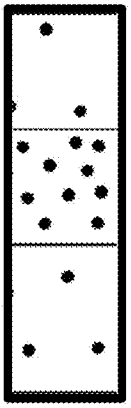
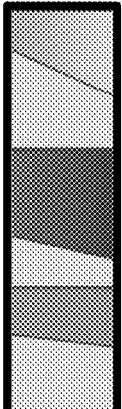
FIG. 13
FIG. 14
FIG. 15

FIG. 18

SYSTEMS, METHODS, AND DEVICES FOR NON-HUMAN READABLE DIAGNOSTIC TESTS

PRIORITY APPLICATIONS

Any and all applications for which a foreign or domestic priority claim is identified in the Application Data Sheet as filed with the present application are hereby incorporated by reference under 37 C.F.R. § 1.57. This application claims priority to U.S. Provisional Patent Application No. 63/202,731, filed Jun. 22, 2021; U.S. Provisional Patent Application No. 63/268,663, filed Feb. 28, 2022; U.S. Provisional Patent Application No. 63/271,996, filed Oct. 26, 2021; U.S. Provisional Patent Application No. 63/264,328, filed Nov. 19, 2021; U.S. Provisional Patent Application No. 63/265,472, filed Dec. 15, 2021; and U.S. Provisional Patent Application No. 63/268,407, filed Feb. 23, 2022, each of which is hereby incorporated by reference herein.

BACKGROUND

Field

The embodiments of the disclosure generally relate to diagnostic tests, and more particularly to systems, methods, and devices for ensuring the integrity of testing processes and results.

Description

Use of telehealth to deliver healthcare services has grown consistently over the last several decades and has experienced very rapid growth in the last several years. Telehealth can include the distribution of health-related services and information via electronic information and telecommunication technologies. Telehealth can allow for long-distance patient and health provider contact, care, advice, reminders, education, intervention, monitoring, and remote admissions. Often, telehealth can involve the use of a user or patient's user device, such as a smart phone, tablet, laptop, personal computer, or other type of user device. For example, the user or patient can administer a health-related test remotely through the user device. Additionally, the integrity of the health-related test will be measured.

Remote or at-home health care testing and diagnostics can solve or alleviate some problems associated with in-person testing. For example, health insurance may not be required, travel to a testing site is avoided, and tests can be completed at a patient's convenience. However, at-home testing introduces various additional logistical and technical issues, such as guaranteeing timely test delivery to a testing user, providing test delivery from a patient to an appropriate lab, guaranteeing timely result reporting from the appropriate lab to a patient, ensuring test result verification and integrity, providing test result reporting to appropriate authorities and medical providers, and connecting patients with medical providers who may be needed to provide guidance and/or oversight of the testing procedures and results remotely.

SUMMARY

Health testing and diagnostics integrity may be important to the administration of medical health and diagnostic tests. In some instances, test integrity may require ensuring that the user is administering the proper test throughout the duration of the test. Unfortunately, this is not always the case. For example, the proper user may not be the individual administering the test, the test may not be valid, there may be test discontinuity, the test instructions may be unclear, there may be user discontinuity, the test may not have physical ease of use, etc. Remote or at home health testing and diagnostics can include tests which can be taken by a patient in his or her own home. In such cases, it may be desirable to have the test integrity measured at various points in time throughout the duration of the test, avoiding the concern for lack of test integrity and the associated problems discussed above.

Embodiments of this application can provide test integrity measurements that can be used to measure or ensure test integrity throughout the duration of the test, for example, having the user provide test identification information such that the information can later be confirmed and validated at various points throughout the duration of the test. In some embodiments, the user may capture and submit information (which can, for example, be image-based, video-based, audio-based, or text-based) regarding the identifying information of the medical diagnostic test with the use of a user device, such as a smartphone, tablet, laptop, or personal computer. In some embodiments, the user may submit this information at more than one point of time during the administration of the test.

For example, a user may make a first submission of test identifying information during a first phase of the administration of the test. Later, the user may be prompted to submit a second submission of test identifying information during a second phase of the administration of the test. A feature detection algorithm may be applied to the submitted information (e.g., the first and second submissions) to detect one or more features therein (e.g., features of medical diagnostic components of a particular type within the images). In some embodiments, the algorithm may determine whether the first and second sets of submissions indicate the same detected feature of a medical diagnostic component in each image. An indication that the same features are detected in each image can provide an indicator of test continuity. In some embodiments, a system can determine whether the user has remained in compliance with the medical diagnostic testing procedure based at least in part on whether the same medical diagnostic component of a particular type is determined to be shown in the first submission and second submission. This can, for example, beneficially eliminate the concern for lack of test integrity regarding remote health and diagnostic testing. This can provide an improved administration of remote or at-home health testing and diagnostics.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

In some aspects, the techniques described herein relate to a computer-implemented method of measuring compliance with a medical diagnostic testing procedure including: providing, by a computing system, a prompt to a user to present a medical diagnostic component to a camera of a user device, wherein the medical diagnostic component is included in a test kit; receiving, by the computing system, a first image captured by the camera; prompting, by the computing system, the user to present the medical diagnostic component to the camera of the user device; receiving, by the computing system, a second image captured by the camera; detecting, by the computing system, a first set of features associated with the first image and a second set of features associated with the second image; determining, by the computing system, if the medical diagnostic component in the first image is the same as the medical diagnostic component in the second image; and based at least in part on the determining, assessing, by the computing system, if the user remained in compliance with the medical diagnostic testing procedure.

In some aspects, the techniques described herein relate to a computer-implemented method, wherein the medical diagnostic test component is a test strip.

In some aspects, the techniques described herein relate to a computer-implemented method, wherein the test strip includes an identifier including any combination of one or more of: a QR code, a pattern, a graphic, an image, or a bar code.

In some aspects, the techniques described herein relate to a method, wherein the identifier is unique to a particular test strip.

In some aspects, the techniques described herein relate to a computer-implemented method, wherein the medical diagnostic test component includes a pattern region.

In some aspects, the techniques described herein relate to a computer-implemented method, wherein the determining includes: determining, by the computing system, a first average color value of the first set of features and a second average color value of the second set of features; and comparing the first average color value and the second average color value.

In some aspects, the techniques described herein relate to a computer-implemented method, further including: determining, by the computing system based on the first set of features, a first identifier; determining, by the computing system based on the second set of features, a second identifier; and determining, by the computing system, if the first identifier is the same as the second identifier.

In some aspects, the techniques described herein relate to a computer-implemented method, further including: determining, by the computing system, a first plurality of identifiers based on the first set of features; determining, by the computing system, a second plurality of identifiers based on the second set of features; and mapping each identifier of the first plurality of identifiers and the second plurality of identifiers to a hash space including hash values.

In some aspects, the techniques described herein relate to a computer-implemented method, wherein mapping each identifier to a hash space includes performing a transformation on at least one identifier of the first and second pluralities of identifiers.

In some aspects, the techniques described herein relate to a computer-implemented method, wherein the transformation includes: color matching, a scale-invariant feature transform, a convolution transform against a template, thresholding, color matching, edge detection, or overlap detection.

In some aspects, the techniques described herein relate to a computer-implemented method, wherein the determining includes: determining a difference in the hash values of the first plurality of identifiers and the hash values of the second plurality of identifiers.

In some aspects, the techniques described herein relate to a computer-implemented method, wherein the difference in hash values is a Hamming distance or a Levenshtein distance.

In some aspects, the techniques described herein relate to a computer-implemented method, wherein the medical diagnostic test component includes a reference region.

In some aspects, the techniques described herein relate to a computer-implemented method, wherein the reference region includes grayscale reference values.

In some aspects, the techniques described herein relate to a computer-implemented method, wherein the reference region includes color reference values.

In some aspects, the techniques described herein relate to a computer-implemented method, wherein the pattern includes a linear pattern, a color gradient, a grayscale gradient, a sine wave, a triangle wave, a square wave, or an arrangement of shapes.

In some aspects, the techniques described herein relate to a computer-implemented method, wherein the medical diagnostic component includes: a first region having a first pattern; a second region having a second pattern; and a third region having a third pattern, wherein the determining includes comparing the first, second, and third regions of the medical diagnostic component of the first image to the first, second, and third regions of the medical diagnostic component the second image.

In some aspects, the techniques described herein relate to a computer-implemented method, wherein the first pattern has a first frequency, wherein the second pattern has a second frequency that is different from the first frequency, and wherein the third pattern has a third frequency that is different from the first frequency and the second frequency.

In some aspects, the techniques described herein relate to a computer-implemented method, wherein the first frequency is larger than the second frequency and the third frequency, wherein the second frequency is larger than the third frequency, and wherein at least one of the ratio of the first frequency to the second frequency, the ratio of the first frequency to the third frequency, and the ratio of the second frequency to the third frequency is not an integer.

In some aspects, the techniques described herein relate to a computer-implemented method, wherein at least one of the ratios is an irrational number.

In some aspects, the techniques described herein relate to a computer-implemented method for diagnostic test result verification including: receiving, by a computing system, diagnostic test information, wherein the diagnostic test information includes a test date and a test result; and generating, by the computing system, a verifiable test result document, wherein the verifiable test result document includes a test result indicator.

In some aspects, the techniques described herein relate to a computer-implemented method, wherein the test result indicator includes an alphanumeric code.

In some aspects, the techniques described herein relate to a computer-implemented method, wherein the test result indicator includes a visible pattern.

In some aspects, the techniques described herein relate to a computer-implemented method, wherein the test result indicator includes a hidden pattern.

In some aspects, the techniques described herein relate to a computer-implemented method, wherein the test result indicator includes an image.

In some aspects, the techniques described herein relate to a computer-implemented method, wherein the test result indicator includes an arrangement of text.

In some aspects, the techniques described herein relate to a computer-implemented method, wherein the test result indicator includes a QR code.

In some aspects, the techniques described herein relate to a computer-implemented method, further including: receiving, by the computing system from a user, a request for test result verification; requesting, by the computing system from the user, the test result indicator; receiving, by the computing system from the user, the test result indicator; determining, by the computing system based on the test result indicator, test result information; and providing, by the computing system to the user, an indication of the test result information.

In some aspects, the techniques described herein relate to a computer-implemented method, wherein the determining includes: extracting, by the computing system from the received test result indicator, query information; and querying, by the computing system using the query information, a database including test result information.

In some aspects, the techniques described herein relate to a computer-implemented method, wherein the indication of the test result information includes any combination of one or more of a test validity status, the test date, the test result, a name of a test taker, a date of birth of the test taker, or an expiration date of the test result.

In some aspects, the techniques described herein relate to a method of determining a non-human readable test result including: receiving, on a test card, a test sample associated with a user; encoding a test result of the test sample on non-human readable result region of the test card; receiving, by a computing system, an first image including the non-human readable result region; receiving, by the computing system, an identifier of the test card; determining, by the computing system based on the identifier of the test card, a decoding key; and determining, by the computing system based on the decoding key and the image of the non-human readable result region, a test result.

In some aspects, the techniques described herein relate to a method, wherein the non-human readable result region includes a grid of cells, wherein each cell of the grid of cells is a control cell, a test cell, or a blank cell.

In some aspects, the techniques described herein relate to a method, wherein the non-human readable result region includes at least control portion and at least one test portion.

In some aspects, the techniques described herein relate to a method, wherein the non-human readable result region further includes at least one blank portion.

In some aspects, the techniques described herein relate to a method, wherein the non-human readable result region includes a gradient, wherein the gradient is indicative of the test result.

In some aspects, the techniques described herein relate to a method, wherein the identifier of the test card includes a serial number visible on the test card.

In some aspects, the techniques described herein relate to a method, wherein receiving the identifier of the test card includes: providing, by the computing system, an interface for inputting the serial number; and receiving, by the computing system, the serial number.

In some aspects, the techniques described herein relate to a method, wherein the interface includes a text input field.

In some aspects, the techniques described herein relate to a method, wherein the interface includes an image capture field for receiving a second image including the serial number, and wherein the method further includes extracting, from the second image, the serial number.

In some aspects, the techniques described herein relate to a method, wherein determine the decoding key includes: applying, by the computing system, a transformation function to the identifier of the card to produce a transformed identifier; querying, by the computing system using the transformed identifier, a database including a plurality of decoding keys; and based on the querying, determining, by the computing system, a decoding key associated with the identifier of the test card.

In some aspects, the techniques described herein relate to a non-human readable test card for a diagnostic test including: a control sensor; a biological test sensor; an integrated circuit; and an antenna.

In some aspects, the techniques described herein relate to a non-human readable test card, wherein the integrated circuit is configured to store a test result of the diagnostic test.

In some aspects, the techniques described herein relate to a non-human readable test card, further including: a result region including the integrated circuit and the antenna; and a test region including the control sensor and the test sensor, wherein the result region is separable from the test region.

In some aspects, the techniques described herein relate to a non-human readable test card, further including: a security mechanism, the security mechanism configured to prevent modification of the stored test result when the result region is separated from the test region, wherein the security mechanism includes a fuse or a wiring arrangement that causes a circuit to be incomplete when the result region is separated from the test region.

In some aspects, the techniques described herein relate to a non-human readable test card, further including a printable battery.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

These and other features, aspects, and advantages of the present application are described with reference to drawings off certain embodiments, which are intended to illustrate, but not limit, the present disclosure. It is to be understood that the attached drawings are for the purpose of illustrating concepts disclosed in the present application and may not be to scale.

FIG. 5 is an example comparison of the distance between first and second hashes for multiple test strips according to an embodiment.

FIGS. 11-15 are medical passports according to some embodiments.

FIG. 18 illustrates grid encoding according to some embodiments.

DETAILED DESCRIPTION

Figure 1:
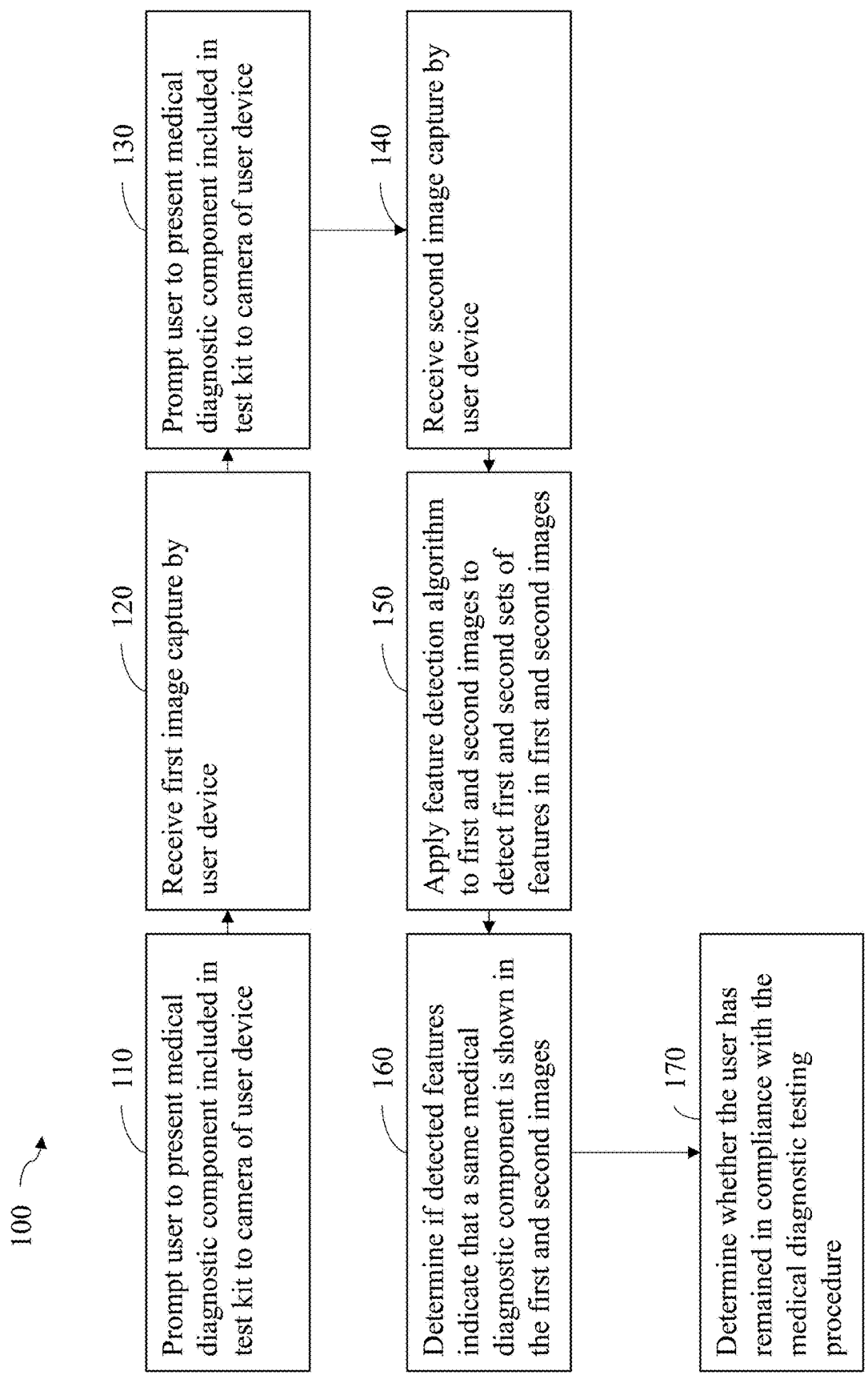
FIG. 1 is a block diagram illustrating an embodiment of a protocol or method for measuring, determining, or maintaining test integrity.

Although several embodiments, examples, and illustrations are disclosed below, it will be understood by those of ordinary skill in the art that the inventions described herein extend beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

As mentioned briefly above and as will now be explained in more detail below with reference to the example embodiments provided in the figures, this application describes devices, systems, and methods for safeguarding testing processes and results, such as health testing or diagnostic integrity and continuity. Embodiments of the inventions described herein can comprise several novel features, and no single feature is solely responsible for its desirable attributes or is essential to practicing the inventions described.

The headings used herein are provided only to aid in understanding the disclosure and are not intended to be interpreted in a limiting manner.

Overview

Remote testing offers many benefits. However, remote testing can present an opportunity for inadvertent or nefarious behavior that results in inaccurate or manipulated results. In some instances, a user or patient may administer a medical, health or diagnostic test, or the like, with the aid of a user device such as a cellphone, smartphone, tablet, laptop, personal digital assistant (PDA), or the like. Such a test may be taken at home or otherwise in the absence of medical professionals. Thus, it can be important to take measures to ensure that a valid test result is obtained.

In some embodiments, the integrity of the test may be measured during administration. For example, test integrity monitoring can include ensuring that the correct user takes a valid test and receives accurate results, that opportunities for inadvertent user error and deliberate cheating are minimized, and so forth. In correspondence to a phase of the test in which the user is setting up the testing materials, collecting their samples, preparing for test administration, etc., the user may be prompted to present a particular type of medical diagnostic component included in a medical diagnostic test kit to a camera of a user device. Such medical diagnostic component may include a test strip, test card, or other test identifying information. A system, such as a remote healthcare or proctoring platform, can be configured to receive a first set of captured information provided by the user on the user device. In correspondence to a phase of the test in which test results may be interpreted, the user may be prompted to present the particular type of medical diagnostic component to the camera of the user device. The system can further be configured to receive a second set of captured information provided by the user on the user device. The system may be configured to apply a feature detection algorithm for detecting at least one feature of medical diagnostic components of the particular type in images within the captured information provided, respectively. The system may further be configured to determine whether the first set and the second set of at least one detected feature indicate that at least one medical diagnostic component of the particular type is the same and shown in the first set of captured information and the second set of captured information. The system may further be configured to determine whether the user has remained in compliance with the medical diagnostic testing procedure based at least in part on whether the same medical diagnostic component of the particular type is determined to be shown in the first set of captured information and the second set of captured information. For example, the comparison can be used to determine if one test strip has been swapped for another during the procedure.

Test integrity is an essential element of remote testing. Accordingly, it may be beneficial to provide a measurement for test integrity, wherein the integrity of the administration of the test can be measured and ensured. This can alleviate concerns that arise from remote testing and can lend to ensuring accurate administration of the test. For example, in some cases, the test may be verified at more than one point in the administration of the test to ensure the same test is administered throughout the testing process. By applying a feature detection algorithm to information captured by the user device at more than one point in time during the administration of the test, the test integrity may be measured.

Various components of the overall test administration process may contribute to test integrity. For example, the user ID may confirm that the person taking the test is the account owner and the one who is in need of the test results. In some embodiments, user continuity may ensure that the same user persists throughout the whole testing process and that they provide their own sample, and not use a proxy (e.g., having someone take a test for them). In some embodiments, the test ID may confirm that the test is valid and that it has not been used before, nor has it expired. In some embodiments, test continuity may ensure that the included test components persist throughout the procedure and that they are not tampered with or exchanged at any point. In some embodiments, results interpretation may contribute to test integrity by making the most accurate results interpretation possible. For example, the user's attestation may be confirmed, and the attestation may be clarified if there are any discrepancies. In some embodiments, test integrity may be dependent on ensuring the user is given the best possible instruction and guidance to allow the user to complete the test correctly, successfully, and accurately. In some embodiments, the test's ease of use may contribute to test integrity. For example, designing the physical test kit and the digital experience in a way that maximizes success for naïve or inexperienced users may ensure test integrity. This includes the design of the test itself, in addition to accessories used (e.g., phone stands, component labeling and handling, test flow, etc.).

Ensuring integrity can be important beyond the testing process. For example, the verification of medical testing results has become increasingly important over time, especially in light of the COVID-19 pandemic. Bars, restaurants, concerts, sporting events, convention centers, hotels, airlines, border crossings, and so forth may, for example, require patrons to show proof of vaccination or proof of a negative test result. This creates significant challenges as the individuals charged with verifying results may be poorly trained to recognize fraudulent documents, and it may be easy for an individual to create a fake document purporting to show, for example, a negative result or that the individual has received a vaccine. At times, individuals may be motivated to provide false results. For example, someone who has traveled to attend an event and tests positive prior to the event may decide to present a false result in an effort to gain entry. In some cases, an employee who is required to take a drug test may be motivated to present false results to their employer. Thus, there is a need for systems and methods that can be used to authenticate test results and ensure that individuals are not presenting false results.

In some cases, the motivation to present a false result or to avoid submitting a genuine result may be especially high. For example, an employee who is required to take a drug test and submit the result may be reluctant to submit the result if they know it is positive, or a would-be concert-goer may be very reluctant to present a result showing that they recently tested positive for COVID-19. Thus, in some cases, it may be desirable for test results not to be readable by the user unless the user submits the result. Such an approach can have other advantages as well, such as ensuring that users receive information relevant to their test result (e.g., treatment information in the case of a positive test result, information about isolating if the user tests positive for an easily transmissible illness, and so forth).

Test Integrity and Continuity

FIG. 1 is a block diagram illustrating an example test integrity measurement protocol or method. The method 100 can be configured to facilitate a measurement of medical diagnostic test administration integrity. The method 100 can be implemented, for example, using one or more components of the system 2300, shown in FIG. 23. Certain steps may be performed on a user device. The user device can be configured to measure the integrity of the test administered, such as the administration of a medical diagnostic test.

At block 110, during a first phase of a medical diagnostic test procedure associated with a medical diagnostic test kit, the system may prompt the user to present a particular type of medical diagnostic component included in the medical diagnostic test kit to a camera of a user device. The first phase may correspond to a phase of the test in which the user is preparing the testing materials, collecting samples, initiating the administration of the test, etc. For example, the medical diagnostic component may include a test card provided in the medical diagnostic test kit, a test strip, a QR code, a barcode, etc.

At block 120, the system may receive a first image captured by the camera of the user device in response to prompting the user in the first phase. At block 130, during a second phase of the medical diagnostic testing procedure that occurs subsequent to the first phase, the system may prompt the user to present the particular type of medical diagnostic component to the camera of the user device. The second phase may correspond to a phase of the administration of the test in which results are to be interpreted.

At block 140, the system may be configured to receive a second image captured by the camera of the user device responsive to prompting the user in the second phase. At block 150, the system may apply a feature detection algorithm for detecting at least one feature of medical diagnostic components of the particular type to the first and second images. This application may detect first and second sets of at least one feature in the first and second images. For example, the features of medical diagnostic components may correspond to features that are present on all test strips (e.g., a pattern that is printed on all test strips, a bar code, a QR code, etc.) Additionally, each feature may exhibit a degree of uniqueness. For example, the way in which the pattern is cropped, designed, or displayed may differ from each previous and subsequent test strip. In some embodiments, such features may include unique codes. Such unique codes may be expected to remain consistent throughout the duration of a given testing session.

At block 160, the system may determine whether at least one detected feature within the first and second set indicate that a same medical diagnostic component of the particular type is shown in the first and second images. Furthermore, a variety of image processing techniques may be involved. Such image processing techniques may include template matching, image comparison, etc. For example, this determination may serve to determine whether the same medical diagnostic component has been used throughout the testing procedure, or whether the user exchanged the original medical diagnostic component with another medical diagnostic component of the same type.

At block 170, the system may determine whether the user has remained in compliance with the medical diagnostic testing procedure. This may be based at least in part on whether the same medical diagnostic component of the particular type is determined to be shown in the first and second images.

Figure 2:
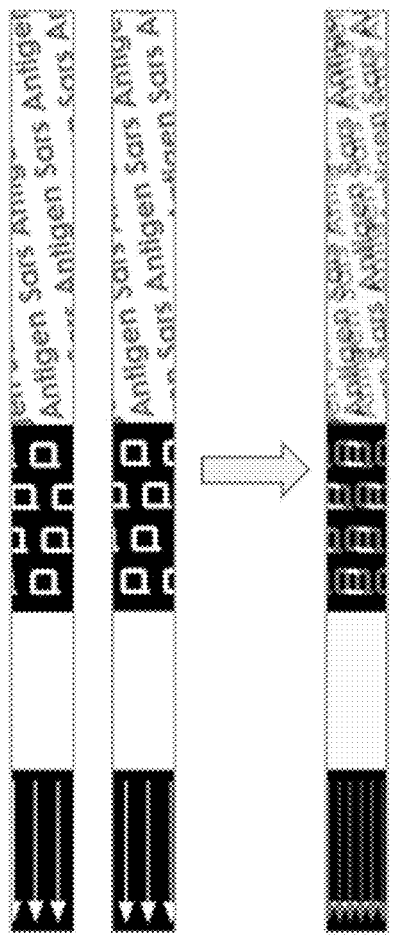
FIG. 2 illustrates an example embodiment of a test strip and how features of the test strip can be analyzed at different points throughout a testing process to determine test integrity and continuity.

FIG. 2 illustrates an example embodiment of a test strip. The test strip may be made in long sheets that are cut to width. In some embodiments, the test strip may include printed patterns that repeat with a different period than the period with which the test strip is cut. This may create a finite or infinite number of unique patterns. For example, when different test strips are overlaid, the patterns may not align as shown in FIG. 2. These patterns can provide a feature which can be detected and analyzed (e.g., at blocks 150, 160) to determine test continuity. For example, if the patterns appear at two different positions at two different time periods of the test, it can be determined that the same testing strip is not being used.

Figure 3:
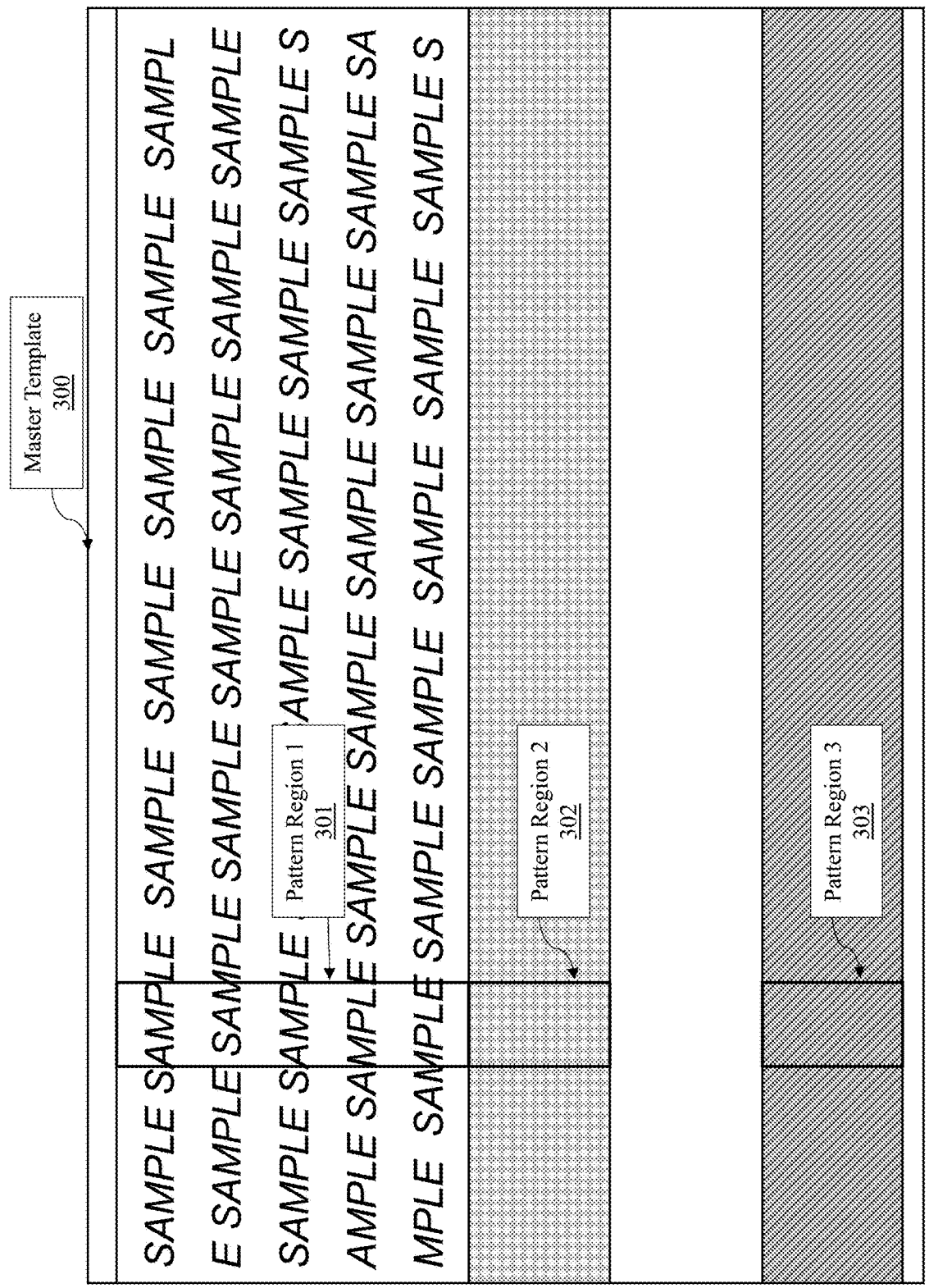
FIG. 3 illustrates an example of pattern regions on a master template according to some embodiments.

As just one example and without loss of generality, in some embodiments, a verification system may collect an image or series of images of a test strip, although other test materials may be used by the verification system. The system may then, using one or more fiducials on the test strip, use a computer vision (CV) algorithm to identify and extract one or more pattern regions. In some embodiments, a pattern region may comprise, for example, squiggles, text, arrows, a random non-repeating element (e.g., a paint splatter), a binary triangle, numbers, characters, or a segment of a photo containing animals, people, manmade objects, natural objects, and so forth. A test strip may have several pattern regions, with the number of pattern regions relating to the distinguishability of different test strips (e.g., more pattern regions tend to correspond to a higher ability to distinguish one strip from another, though this need not always be the case). For example, FIG. 3 illustrates an example of various pattern regions on a master template 300. In FIG. 3, a master template 300 (which may be, for example, a large sheet that will later be cut into test strips) may contain a first pattern region 301, a second pattern region 302, and a third pattern region 303.

Within each pattern region, the CV algorithm may extract one or more identifiers. Identifiers may be, for example, the horizontal location of a pattern region with respect to a larger master template, the vertical location of a pattern region with respect to a larger master template, an average color of the pattern region, a number of features (such as paint speckles) in a pattern region, characters in a pattern region determined by optical character recognition, a ratio of black to white coverage in a region (which may be determined with or without automatic or manual binarization), and so forth. It will be appreciated that different identifiers may be applicable to different pattern regions. For example, in FIG. 3, the varying alignment of the text in the first pattern region 301 could give an indication of the distance from the left edge of the master template, but such an indication may be of limited utility in the second pattern region 302 and the third pattern region 303 because those pattern regions contain patterns that repeat horizontally across the master template 300. Moreover, while the pattern regions in FIG. 3 correspond to different individual patterns, a pattern region may contain more than one pattern. For example, a pattern region could combine the second pattern region 302 and the third pattern region 303. In some cases, combining patterns could allow for additional identifiers. For example, if a pattern region contains two patterns with different horizontal periods, it may be possible to identify a location along the horizontal axis of the master template.

Figure 4:
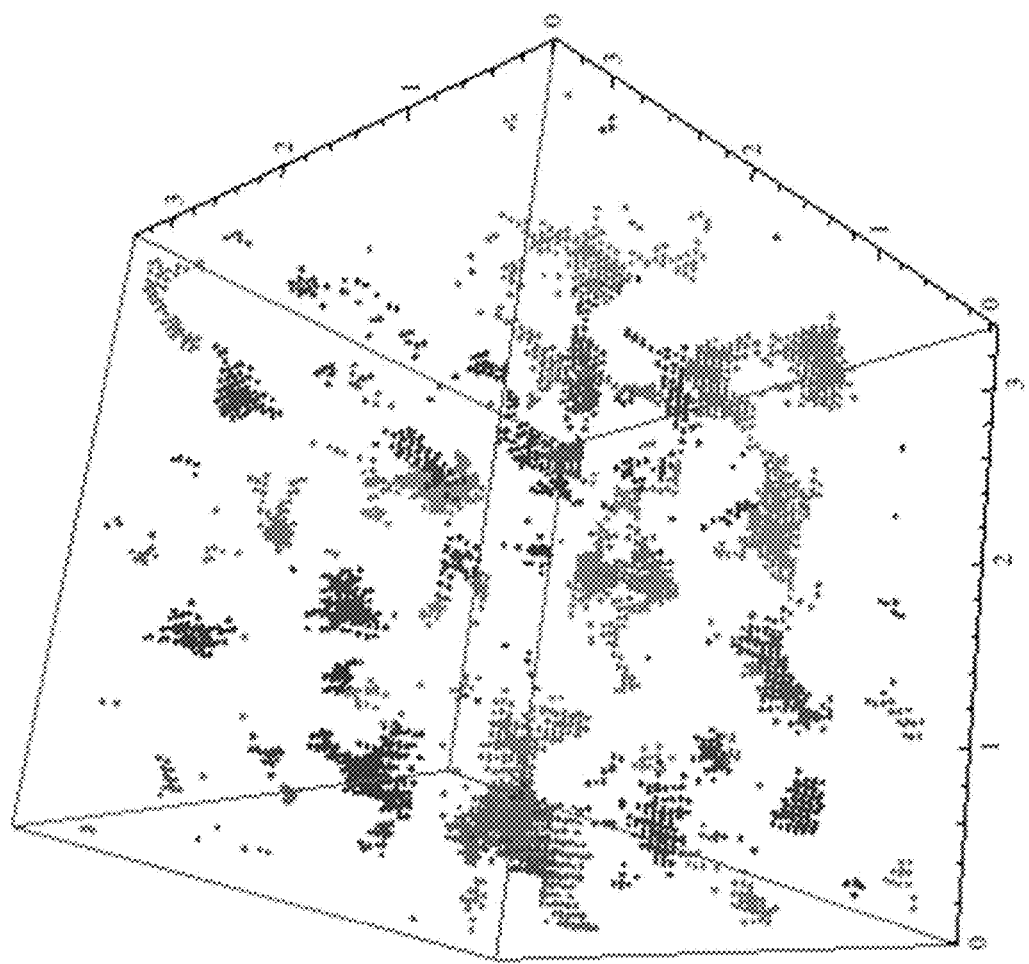
FIG. 4 is an illustration of a hash outcome space according to some embodiments.

In some embodiments, each identifier may be mapped onto a different orthogonal axis in hash outcome space. As an example, FIG. 4 shows an example of hash outcome space mapping for the relatively simple case of three orthogonal axes (e.g., three identifiers). A hashing algorithm may be used to generate the mapping into hash outcome space. The hashing algorithm may, for example, comprise scale-invariant feature transforms, thresholding and convolving a region against a template to determine a match quality, multi-scale template matching, automatic binary thresholding, white-balance corrected color calculations, edge detection, overlap detection against a master template, and so forth.

As one example and without loss of generality, in some embodiments, each identifier may be mapped to a number 0 through 9. In the case of three pattern regions, each having two identifiers, there are six total identifiers, each of which can have ten possible values, meaning there are one million possible combinations of identifier values. These one million possible combinations may be called hashes or may undergo a further transformation to create a hash. It will be understood that a particular test strip does not have to match up exactly with the one million possible values. Rather, the one million possible values indicate the number of meaningfully different groups or clusters of identifiers that may be distinguished.

In some embodiments, it may be advantageous for the verification system to capture multiple images of the test strip. Each image may be plotted in hash outcome space. A clustering algorithm may then be used to identify a center for the different hashes, and this center may be used to identify the strip.

At a later point in the testing procedure, the above process may be repeated using a second image capture or set of image captures. In some embodiments, a difference may be determined between the hash for the first set of images and the hash for the second set of images. For example, in some embodiments, the system may calculate a Hamming distance, Levenshtein distance, or the like. If the strip presented in the first set of images matches the strip presented in the second set of images, the distance should be small.

As shown in FIG. 5 for a comparison of five test strips in an idealized scenario, the Hamming distance between the first and second hashes for the same strip should preferably be zero (e.g., the first hash and second hash should be the same), while comparisons of different strips should give a comparatively large distance (in the example of FIG. 5, the maximum distance has been normalized to one). It will be appreciated that different strips may have Hamming distances less than the maximum distance. For example, the patterns on one test strip may be very similar to the patterns on another, different, test strip. A sufficiently robust hashing approach should be able to distinguish between the same and different test strips with few false positives or false negatives (e.g., the system should not identify a mismatch when the strip has not been changed, nor should the system identify a match when the strip has been changed).

In some embodiments, additional features of the test strip may be used. For example, the test strip may have a lot number, batch number, serial number, date of manufacture, or the like, which may further help to verify that the strip presented in the first set of images is the same as the test strip presented in the second set of images.

Figure 6:
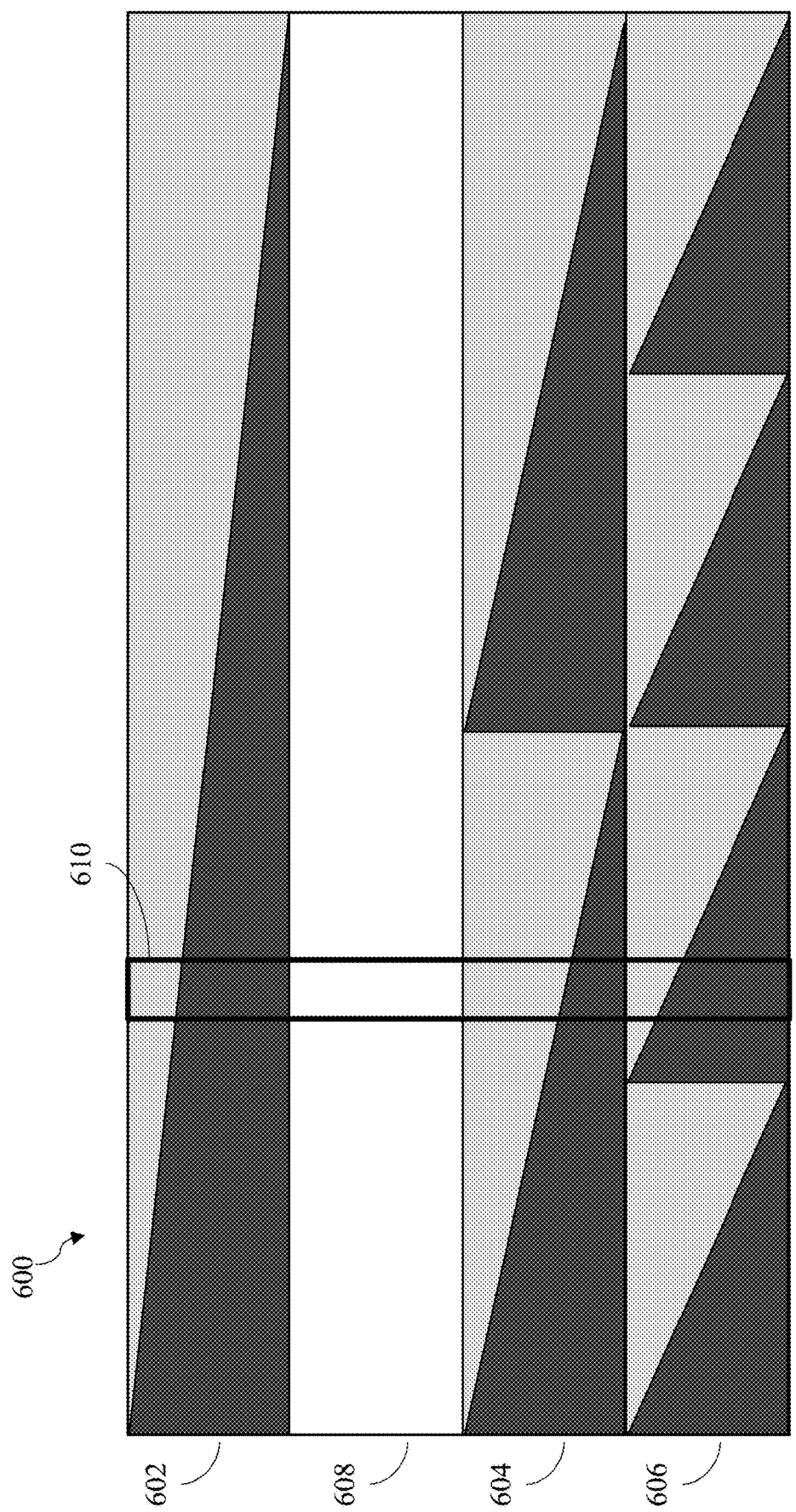
FIGS. 6-10 are example embodiments of patterns that may be used to determine test integrity.

As discussed above, components such as test strips may be imprinted with one or more patterns that make it possible to differentiate between individual test strips. The particular features of patterns can make identifying and differentiating between two components more robust. For example, FIG. 6 depicts a master 600 from which a test strip 610 may be cut. The master contains a first pattern region 602, a second pattern region 604, a third pattern region 606, and a lateral flow region 608. Considering the patterns shown in FIG. 1, it is possible to determine the horizontal position of the test strip 610 by, for example, determining the percentage of light gray in the first pattern region 602. For example, the percentage of light gray in the first pattern region 602 is about 63% in the example given in FIG. 1. As depicted in FIG. 1, the second pattern region 604 and third pattern region 606 are not strictly necessary for determining the test strip 610's position within the master 600. For example, the location of the test strip 610 could be determined by looking at the percentage of light gray in the first pattern region 602. However, the additional patterns in the second pattern region 604 and the third pattern region 606 may enable more robust determination of the location. For example, the pattern in pattern region 602 changes gradually across the width of the master 600. Thus, due to errors in manufacturing and in measurement, adjacent strips may have similar hashes if only the first pattern region 602 is considered. The second and third pattern regions 604 and 606 change at twice and four times the rate of the first pattern region 602, respectively, and thus they may be used to better determine the location of the test strip 610 within the master 600. As just one example, the test strip 610 may have a hash of (23, 67, 18), corresponding to the percentage of light gray in each pattern region.

As depicted in FIG. 6, each time the master 600 is repeated, the patterns also repeat. For example, if a master 600 can hold twenty test strips, then every twentieth strip will have the same hash. This can result in many hash collisions, undermining confidence that comparing a first hash and a second hash can reliably determine whether a test component has been exchanged during a testing procedure. This problem can be alleviated by changing the relative periodicity or frequency or the patterns in the first, second, and third pattern regions. For example, in FIG. 6, the pattern in the second pattern region 604 has a period twice that of the pattern in the third pattern region 606, and the pattern in the first pattern region 602 has a period twice that of the pattern in the second pattern region 604. This causes the pattern to repeat frequently. Instead of having the periods (or frequencies) of the different patterns be whole integer multiples of each other, it is advantageous that the period (or frequency) ratios are not whole integers, and preferably are irrational. For example, in the case of two pattern regions, if the first pattern repeats every 7" and the second pattern repeats every 6", then the overall pattern (e.g., the first pattern and second pattern together) only repeats every 42", or after six iterations of the first pattern and seven iterations of the second pattern. In this example, if the master is seven inches so that one whole iteration of the first pattern appears on each master, then there would be a repeat only every seventh sheet, or every 140th test strip if each sheet holds twenty test strips. Preferably, the ratio of the first pattern to the second pattern is irrational (for example, $\pi$, e, or $\sqrt{2}$), in which case the pattern never repeats and the only opportunity for hash collisions arises from errors in determining hash values.

Figure 7:
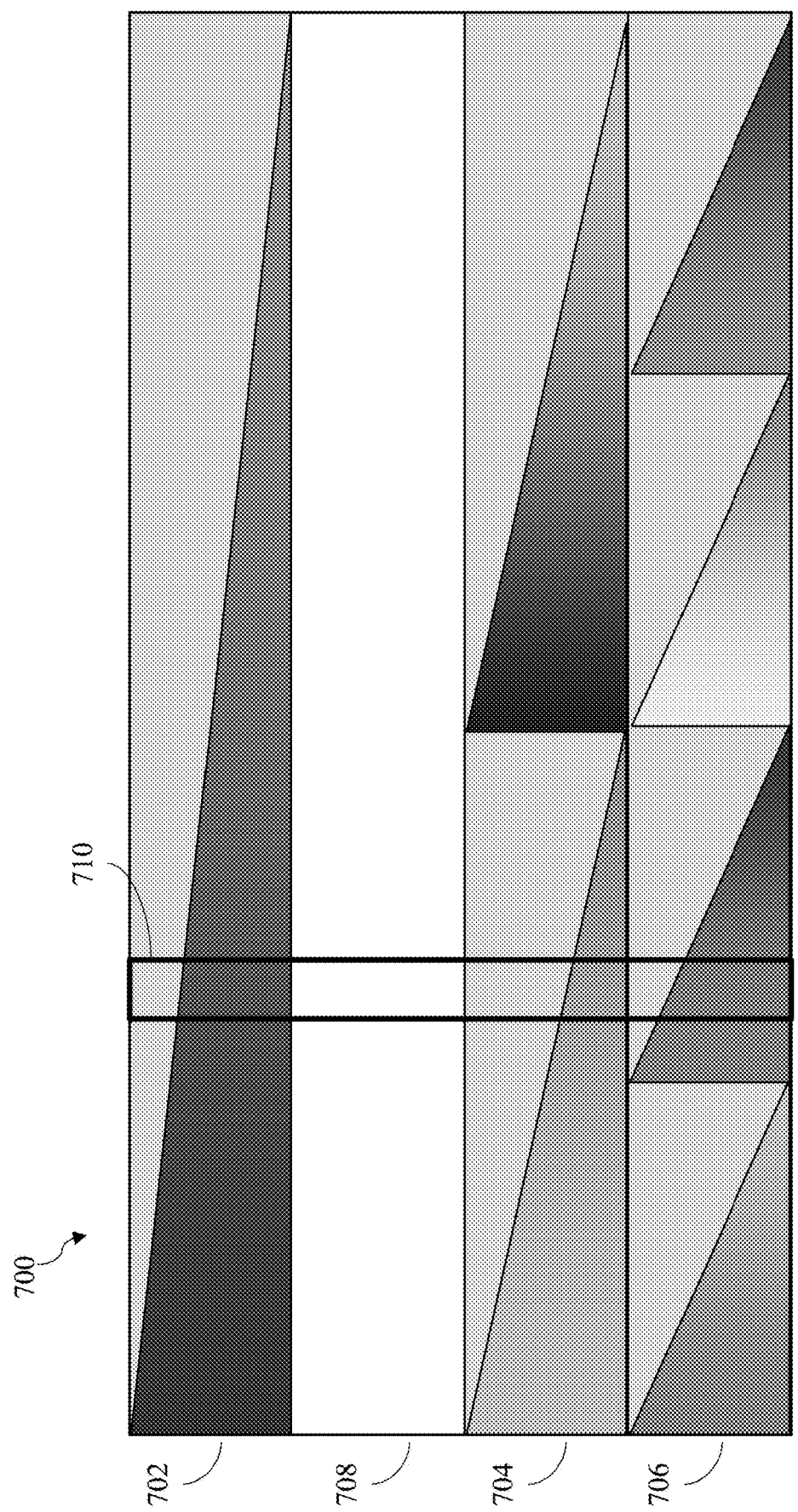

The robustness of the hash may be further increased by adding additional features to the patterns. For example, instead of light gray and dark gray, the dark gray regions could instead contain color gradients, as depicted in FIG. 7 (which shows the color gradients in grayscale), illustrating a test strip having pattern regions 702, 704, and 706, and lateral flow region 708. The hash for FIG. 7 could then comprise additional components. For example, instead of percentage light gray alone, the hash could also use the color in each pattern region. For example, the test strip 710 may have a hash of (23, red, 67, blue, 18, green), representing the percentage light gray and the color in the first, second, and third pattern regions 702, 704, and 706. The additional information used to determine the hash may increase accuracy of the strip identification and reduce the likelihood of collisions that may arise from errors in hash determination.

Figure 8:
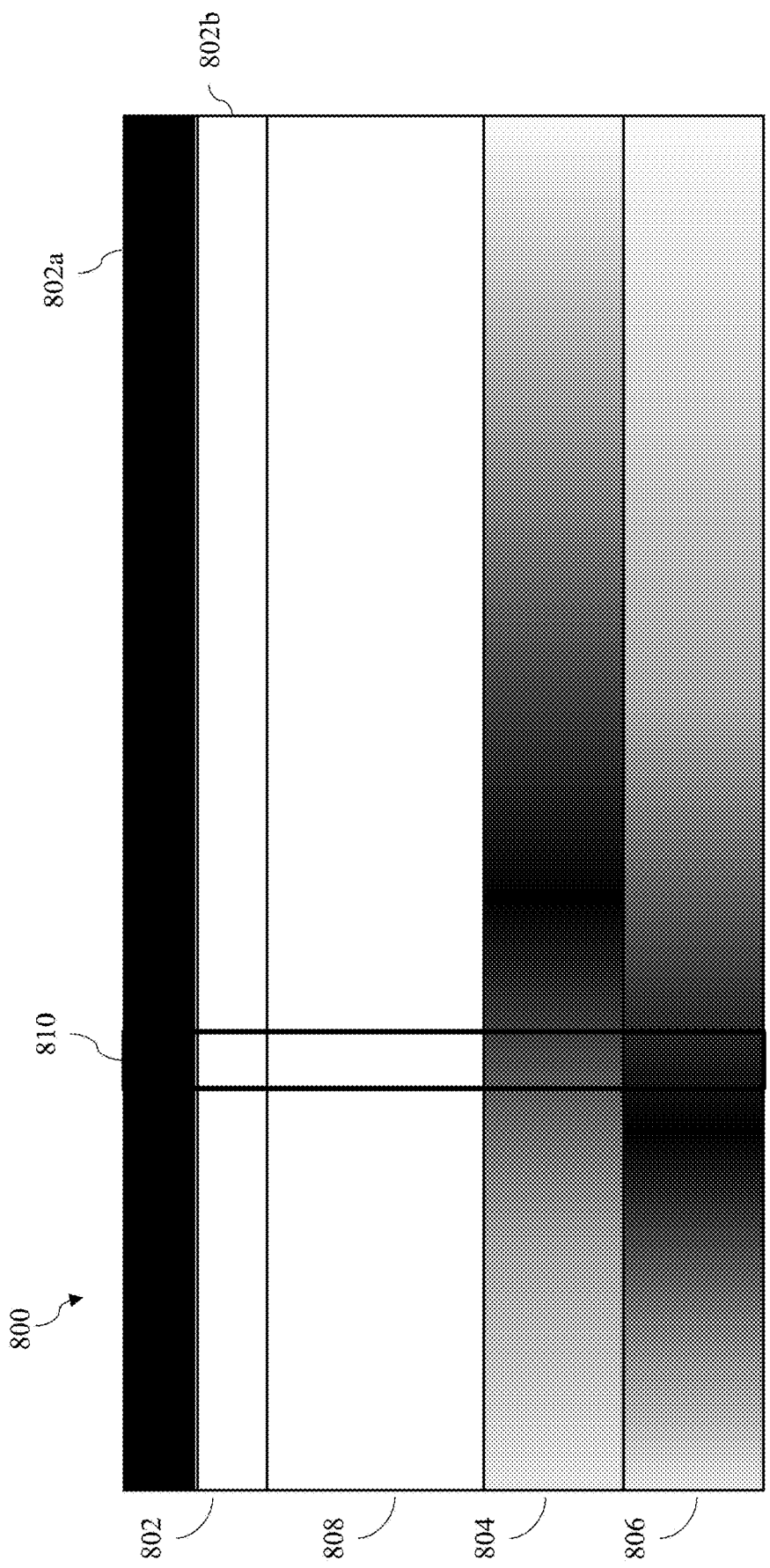

In some embodiments, it may be beneficial to have one or more reference regions. Reference regions are useful because, for example, they can be used to determine and account for the effects of poor lighting, poor color accuracy of a camera, and so forth. For example, if color is used to determine a hash, it may be beneficial to have regions that contain known color values (for example, strips of pure red, pure green, and pure blue). This may enable more accurate color determination, resulting in more robust hashes. For example, considering once more FIG. 7, if color reference regions are added to the master 700, then it may be possible to determine more precise color values. For example, instead of determining that the color in the first pattern region of the strip 710 is "red," a system may determine a particular color value (e.g., RGB value, CMYK value, or the like). Similarly, if a hash uses brightness (or percent gray) to determine a hash, it may be beneficial to have a reference region that can be used to determine white and black values and possibly other values such as, for example 50% gray. For example, FIG. 8 depicts a master 800 having a lateral flow region 808 with a reference region 802 containing a first reference strip 802a and a second reference strip 802b which may be used to determine black levels and white levels. The first pattern region 804 and the second pattern region 806 may contain, for example, grayscale gradients. The information obtained from the reference region 802 may be used in conjunction with gray level values associated with the first pattern region 804 and the second pattern region 806 of the test strip 810 to determine a hash for the strip 810. Without the reference regions, uncertainty in the gray level values of the first pattern region 804 and the second pattern region 806 could result in significant uncertainty in the location of the strip 810 within the master 800, especially when tests are performed by end users at home in conditions using suboptimal conditions and equipment (e.g., bad lighting, poor quality cameras).

Figure 9:
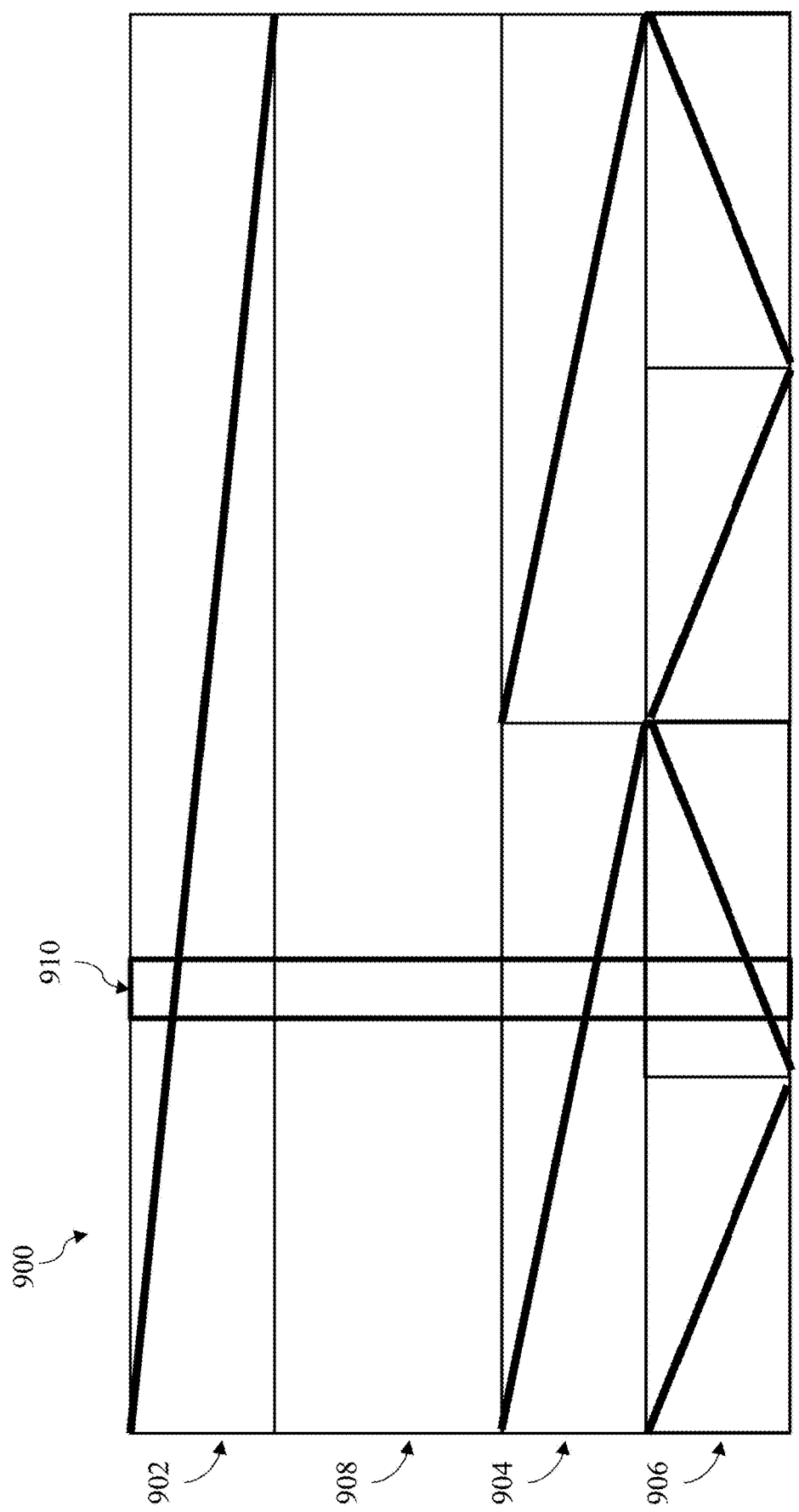
Figure 10:
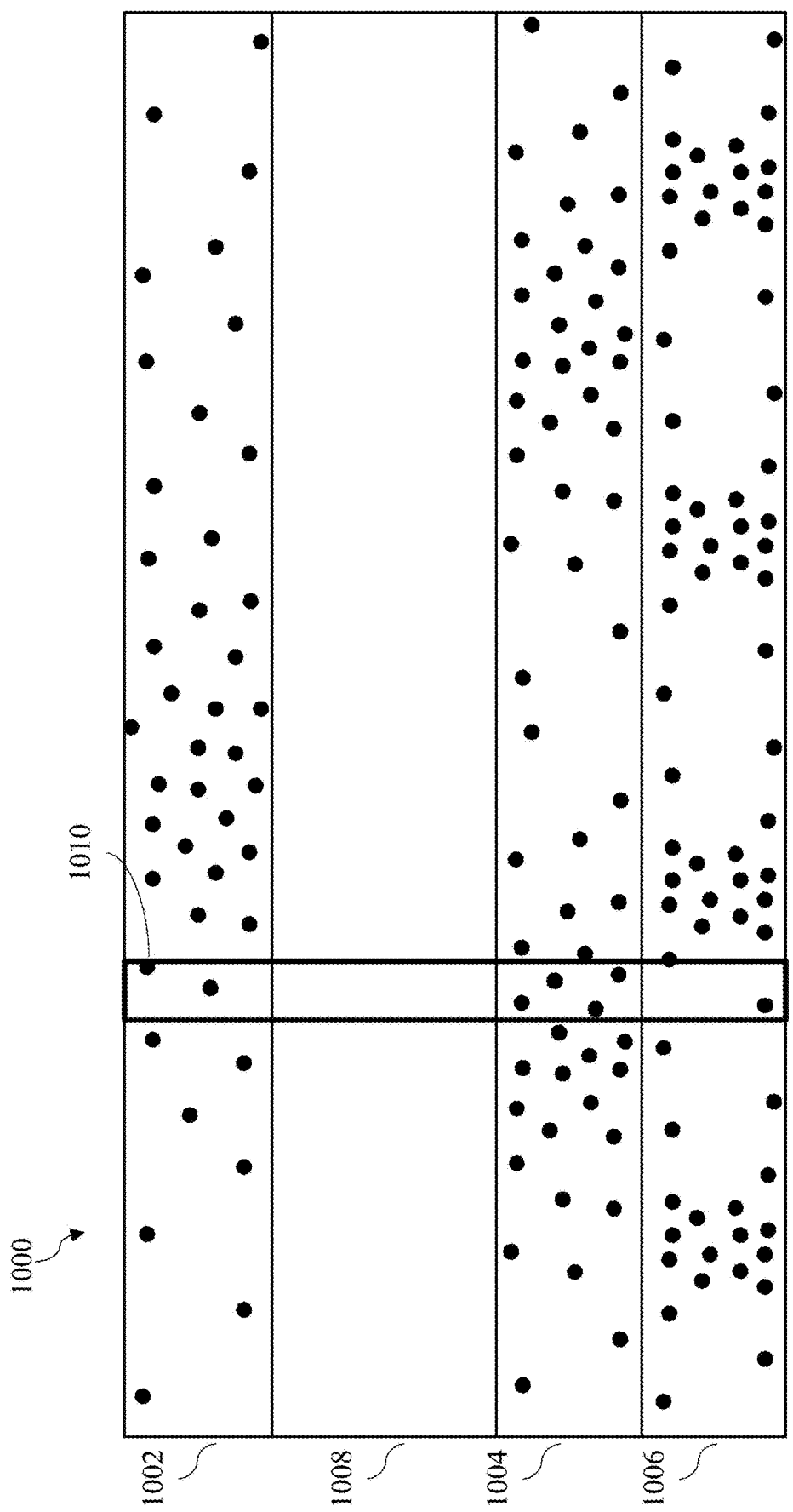

While colors and gradients were used in the above examples, it will be appreciated that other patterns could be used. For example, hashes could be determined based on the vertical locations of lines in one or more pattern regions, or they could be based on pattern density gradients. In some embodiments, a pattern may be a linear pattern, a sinusoidal pattern, a triangle wave pattern, a square wave pattern, and so forth. FIGS. 9 and 10 depict examples of using line location and pattern density, respectively. In FIG. 9, a master 900 has first, second, and third pattern regions 902, 904, and 906, and lateral flow region 908. A hash value for the test strip 910 may be, for example, (0.7, 0.4, 0.3), corresponding to the average vertical location of the lines in the first pattern region 902, the second pattern region 904, and the third pattern region 906. In FIG. 10, a system may determine a hash value by counting the number of black dots on the test strip 1010 of a master 1000 having a lateral flow region 1008 within each pattern region 1002, 1004, and 1006. In some cases, dots may only be partially within the test strip 1010. The system may be configured to count or discard partial dots according to some criteria. For example, partial dots could be always counted, always discarded, or counted based on the amount of the dot that is on the test strip 1010. For example, in some embodiments, a dot may be counted if more than half the dot is within the test strip 1010. For example, in FIG. 10, the test strip 1010 may have a hash of (2, 4, 1), corresponding to the number of dots in each pattern region, where the partial dot in the third pattern region 1006 has not been counted.

While the examples above focus on the use of patterns to identify strips used in lateral flow tests, the skilled artisan will appreciate that the present disclosure has many potential applications. For example, patterns may be applied to other test components or may be used in different contexts. Several advantages may be realized by use of the present disclosure. For example, patterns may be used in some contexts to replace traditional barcodes, alleviating the need to generate and print codes. The present disclosure may also enhance security. For example, it is possible to implement a unique hashing algorithm that is unknown to others. It may also be useful in, for example, double blind experiments to have an ad hoc tag that no one has a priori knowledge of (as opposed to, for example, a generated barcode). Patterned tags may be used for arbitrary tracking purposes. For example, end users may have a sticker roll or sheet of patterned tags that can be used to tag items. For example, a user may apply a patterned tag sticker to a saliva collection tube and scan the sticker before submitting the sample to a lab for processing. A lab may then scan the received sample and associate the sample with the user. Outside of the health testing context, patterned tag stickers could similarly be used for merchandise returns. Patterned tags may also be used as a form of identification or validation. For example, patterned tags may be used as part of an employee ID instead of a barcode, RFID chip, or the like, or patterned tags may be used to validate tickets for an event. In some embodiments, retailers and brands may take advantage of the present disclosure to improve product packaging. For example, barcodes on products could be replaced with pictures, patterned logos, and the like.

Test Result Integrity

In some cases, a provider of testing services, which may facilitate testing at a medical facility, at a patient's home, or at another location, may provide the patient with documentation of the patient's test results. For example, the provider may make a medical passport available to the patient, which the patient can present whenever proof of a test result is needed. In some cases, verification may be performed by a human, may be automated, and performed by a machine, or may be performed by a government body. In some embodiments, a passport may be created with one or more features that allows the passport's authenticity to be verified. For example, a passport may include a barcode, QR code, or other indicator that directs a user to a web page for verification of test results. A human could scan the code and check the results on the page, or a machine could be configured to automatically parse the results from the web page. In some cases, a server may respond with a web page, while in other embodiments, the server may respond with JSON, XML, or in some other suitable manner for verification. While the web page can be used to verify results, it is important that the web page itself can be verified as authentic. For example, the web page may preferably operate using hypertext transfer protocol secure (HTTPS) and the server may have a certificate indicating the source of the web page.

Figure 12:
Figure 11:
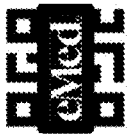

FIG. 11 depicts a passport according to some embodiments. In FIG. 11, basic information about the patient is displayed alongside information about the test and the result of the test. The passport includes a QR code that links to a web page where the test result can be verified. FIG. 12 depicts another passport according to some embodiments. In FIG. 12, the passport contains visual indications of the source of the passport. For example, a logo or other artwork may be embedded within a QR code or may be placed in other locations on the passport. In some embodiments, a system may use computer vision to recognize the artwork to aid in verifying the passport's authenticity. In some embodiments, a set of rules that the art must abide by may be used as a further means of verification. For example, a testing provider may implement undisclosed rules on the sizing, placement, and so forth of artwork.

FIG. 13 depicts a passport according to some embodiments. In FIG. 13, the passport again contains basic information about the user and the test, but now also includes a verification code. For example, someone who wishes to verify the passport may scan the QR code and may be prompted to input the verification code or may be shown a verification code to compare to the code shown on the passport.

FIGS. 14 and 15 depict passports according to some embodiments. In FIGS. 14 and 15, a verification pattern is shown on the passport. For example, the verification pattern can be a series of colors or gradients disposed inside shapes or segments, or the verification pattern can be an arrangement of dots. These are merely examples, and other graphical representations may be used as verification patterns. For example, verification patterns may include shapes, colors, repeating patterns, landscapes, and so forth, so long as the verification pattern can be recognized by a computer vision system.

The use of non-standard patterns may strengthen fraud prevention. For example, individuals who would create fraudulent passports may not understand how to decode the pattern or how to generate a new, meaningful pattern. In some cases, it may not be apparent that there is a code embedded in the passport. For example, a code could be hidden in the placement of text, images, and other features on the passport, rather than having a clearly-identified region that corresponds to a code.

In some embodiments, a QR code may link to a verification page. The verification page may prompt the user to enter one or more pieces of information from the passport. For example, the user may be prompted to enter the passport bearer's name, date of birth, and so forth. Alternatively, or additionally, the user may enter a verification code, such as an alphanumeric string, that may be embedded in the passport.

Figure 16:
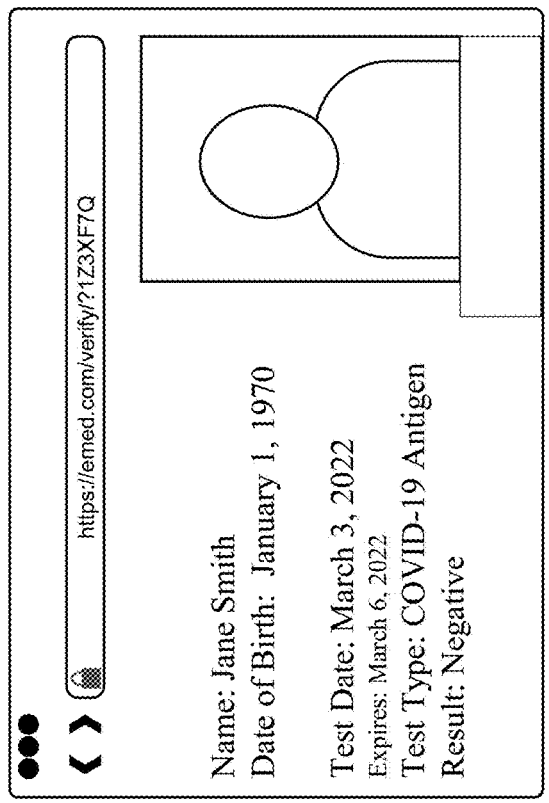
FIG. 16 is a passport verification screen according to some embodiments.

In some embodiments, a QR code may directly link to test results. For example, a code may be customized for each user and embedded into that user's passport, and scanning the code may, for example, open up a web page that shows the test date, test result, user's name, and so forth. FIG. 16 depicts a web page that may be displayed upon scanning a code. The web page may contain similar information to what is contained on the passport. The web page may also include an image of the user. The image may have been captured during an at-home testing session, for example by a webcam while the user was performing the testing procedure. Someone verifying the passport may compare the results on the verification page with the results shown on the passport and may compare the photo on the web page with the appearance of the individual presenting the passport. In some cases, the web page may display an expiration date for the test result. For example, a test result may expire after a day, several days, a week, or some other period of time, which may depend on location (for example, different local governments may implement different rules), type of test, and so forth. In some embodiments, the web page may display a test validity status (e.g., a binary indication of whether the test result is valid).

Figure 17:
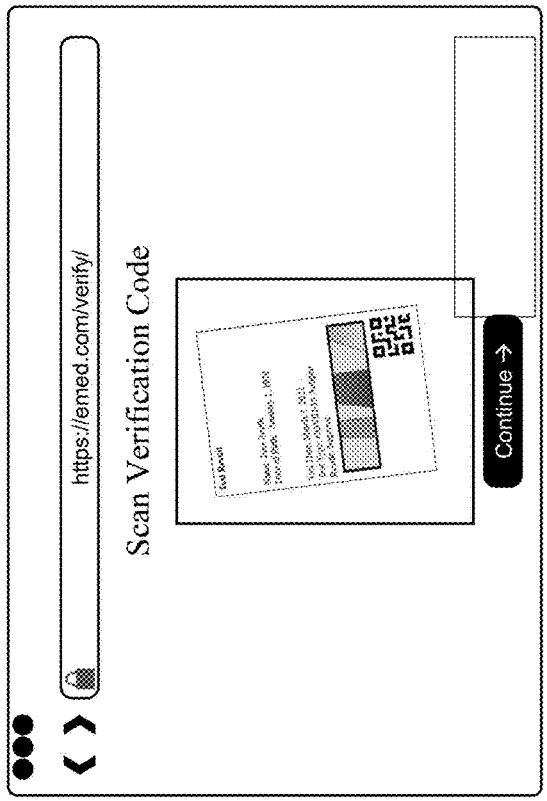
FIG. 17 is a passport verification code capture screen according to some embodiments.

Alternatively, a code may be embedded that takes the user to a verification page where additional information can be entered. An example is shown in FIG. 17. An individual may be prompted to scan the passport or a portion of the passport in order to retrieve a results page, such as the page shown in FIG. 16. This may be advantageous because, for example, it allows for highly customized verification codes to be embedded in the passport, rather than being limited to codes that devices natively support, such as QR codes. As discussed above, the use of complex or obfuscated codes may provide additional security.

Non-Human Readable Test Results

In some cases, it may be desirable for users or patients not to have immediate access to test results. For example, some tests may be vulnerable to misinterpretation by users and/or proctors. In some cases, non-human readable test results can help ensure that users or patients upload their results to a medical testing platform. Machine-readable results can be used to encourage a user to use an application or online platform for viewing results. In some cases, an online platform can provide information based on the test results and/or connect the user to follow-up care.

In some embodiments, a system may be configured to encode a test result in a grid and/or other pattern. In some embodiments, each section of the grid can be a control indicator, a test indicator, and/or a blank. In some embodiments, a system can be configured to have multiple encodings. In some embodiments, an encoding selection may be based on a property of the test, for example a serial number on a test card, which can be read using computer vision techniques such as recognizing printed letters, numbers, and/or symbols on the test card. In some embodiments, a QR code and result can be read in a single image. For example, the QR code may act as an identifier of the test. Thus, the key for decoding a test result can vary from test card to test card, thereby making it difficult or infeasible for a person to FIG. out how to decode test results.

In some embodiments, the systems and methods disclosed herein leverage current technology such as monochrome dyes and nitrocellulose backers. In some embodiments, a test serial number (or other identifier) and test result can be read from a single smartphone image, for example using computer vision and/or optical character recognition technology. In some embodiments, more complex implementations may be used. In some embodiments, some, most, or all results are ambiguous without a key. In some embodiments, at least some results are knowable if a user learns the key. In some embodiments, different SKUs or other identifiers of the test strip and code may be tracked so that some can be read by humans while others cannot. For example, a test could be sold both in versions that can and cannot be readily read by humans. However, this can add manufacturing and supply chain complexity.

Figure 18:
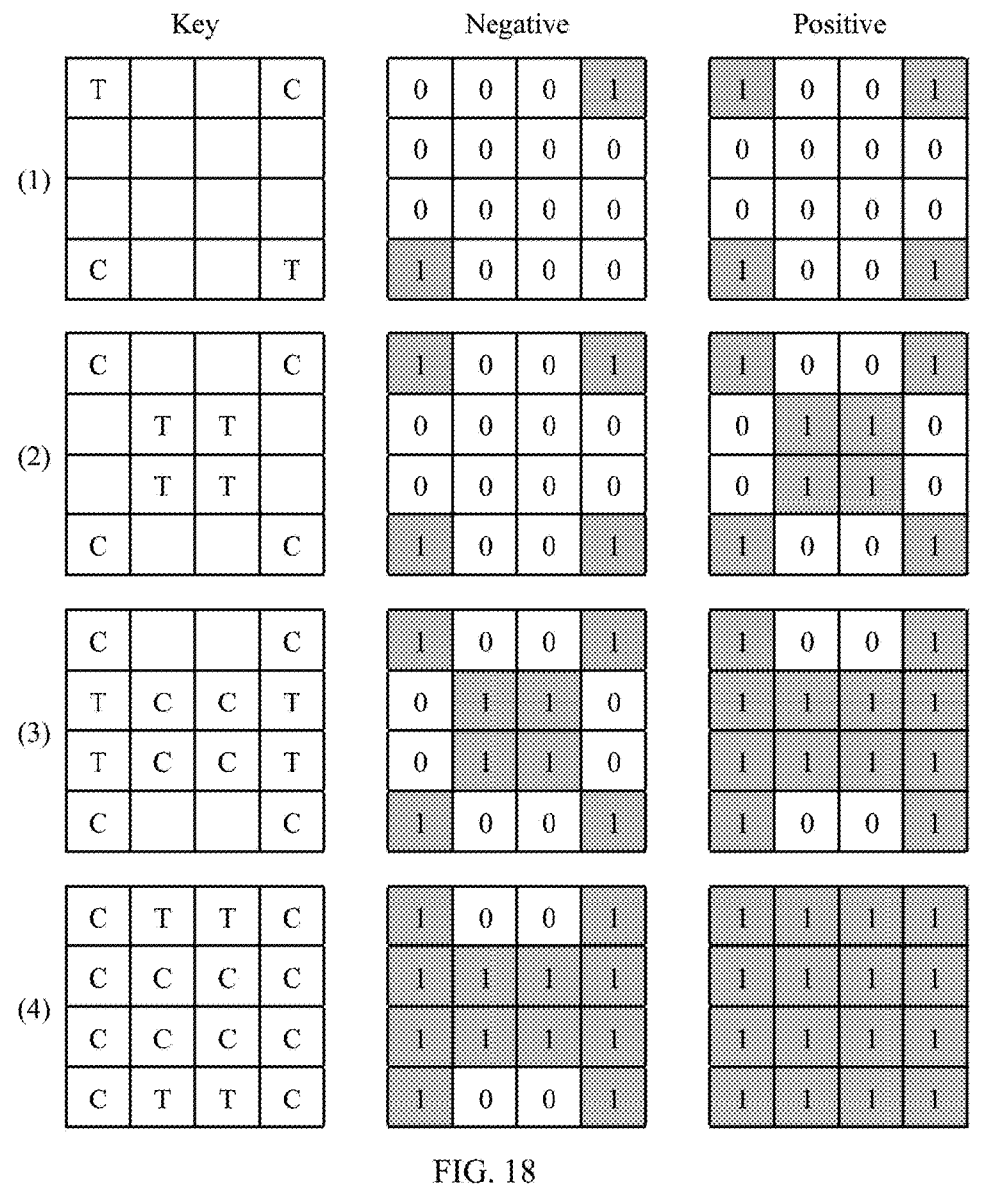

As discussed briefly above, in some embodiments. grid encoding can be used. FIG. 18 illustrates grid encoding according to some embodiments. As shown in FIG. 18, a grid can have test cells (that are only changed when a result is positive) and control cells (that change whenever a valid test is performed) arranged at various locations. As shown in FIG. 18, various keys can be used, and a positive test result for one key can appear the same as a negative test for another key. For example, a positive test for key (1) looks the same as a negative test for key (2). Likewise, a positive case for key (2) looks the same as a negative case for key (3), and a positive result for key (3) looks the same as a negative result for key (4). Thus, for these, without knowing the key, an individual would have no way of readily determining whether a test result was positive or negative. However, a negative test for key (1) and a positive test for key (4) do not have corresponding positive and negative results for other keys. Thus, an individual could discern that these represent positive and negative test results, e.g., that a key (1) negative result is negative, and a key (4) positive result is positive, even without knowing the keys.

Figure 19:
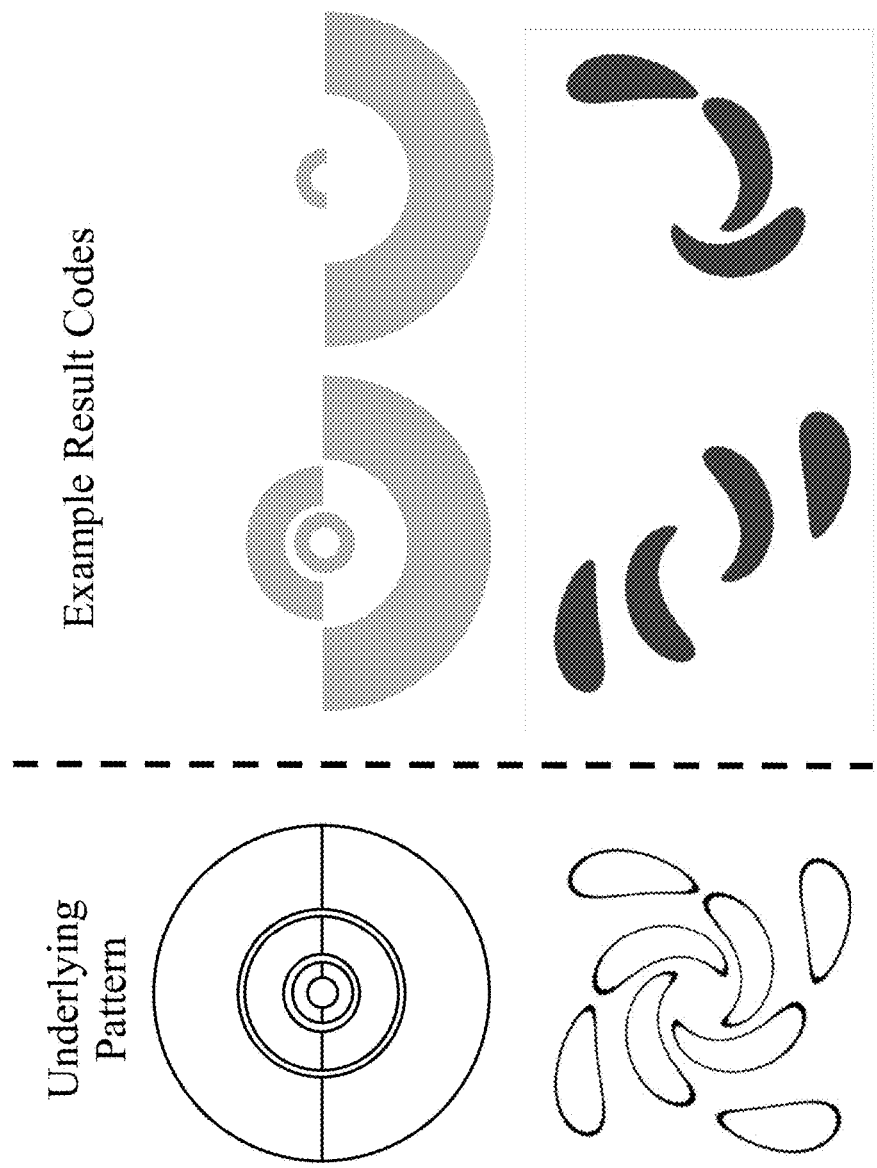
FIG. 19 illustrates example pattern encodings according to some embodiments.

In some embodiments, rather a grid pattern, spirals or other patterns can be used. It may be more difficult for an individual to discover the underlying pattern, which can increase the difficulty of decoding results. For example, humans may be able to readily discern a grid or other simple pattern, but may not immediately recognize more complex patterns, especially when only part of the pattern is visible. Advantageously, computer vision systems may be able to easily recognize patterns where humans may struggle. FIG. 19 depicts two example patterns. As can be seen in the example result codes, the underlying pattern may not be readily apparent to a user. Patterns can be more or less complex and can require more or less time, trial, mental effort, and so forth for a human to figure out.

The example embodiments depicted in FIGS. 18 and 19 show patterns that are visible to users, but which cannot be easily decoded without knowing a key that corresponds to a test result. In some embodiments, techniques may be used that make the test result invisible or barely visible to a user while being visible to a smartphone camera or other image capture device. For example, a colored dye that is normally visible with the naked eye can be replaced by a dye that reflects in the infrared or ultraviolet regions of the electromagnetic spectrum. In some embodiments, a fluorescent or retroreflective dye may be used that can be seen briefly with a camera flash. In some embodiments, a very faint dye or gradient that is nearly invisible to the naked eye can be used, so long as a system can image the dye or gradient and extract the result using image processing techniques. Although embodiments described herein can prevent easy reading of results by individuals, a determined user may be able to extract results, for example by capturing one or more photographs and, optionally, performing one or more image processing steps.

In some embodiments, faint gradients may be used to encode results. In some embodiments, a negative result may not have a gradient, but a positive result may have a gradient, although other configurations are possible. For example, in some embodiments, a positive result may not have a gradient and a negative result may have a gradient, or positive and negative results may both have gradients that are different from each other. In some embodiments, a gradient may be too faint for a human to detect with the naked eye, but a computer vision system may be able to detect the gradient. In some embodiments, results can be encoded as an intensity variation, a periodicity, a phase (e.g., a vertical and/or horizontal offset in a pattern), and so forth.

Figure 20B:
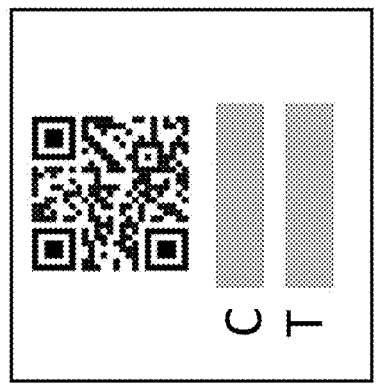
FIG. 20B illustrates a test card according to some embodiments.
Figure 20A:
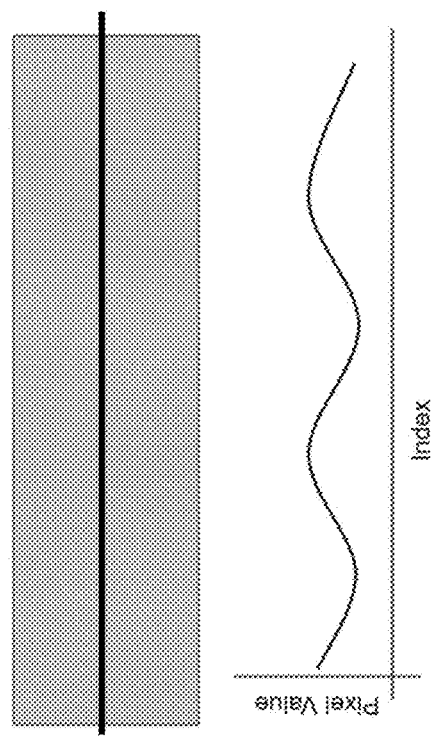
FIG. 20A shows a strip with a faint gradient according to some embodiments.

FIG. 20A shows a strip with a faint gradient according to some embodiments. With the naked eye, the strip appears to be a solid color. However, as indicated in the plot below the strip, the color value (or gray value) can vary slightly across the strip. This variance can be readily detected using computer vision methods. FIG. 20B illustrates a test card according to some embodiments. The test card contains a QR code which can include, for example, a serial number or other identifier. The test card includes a control strip and a test strip. In some embodiments, the control strip, and the test strip both use patterns. In some embodiments, only one of the control strip and the test strip use patterns. In some embodiments, the control strip and test strip can use the same pattern or different patterns.

In some embodiments, instead of (or in addition to) visual patterns, a test card may use RFID tags or other technologies. RFID tags can be readily read by many modern smartphones, and thus can be a good candidate for use in a test card. In some embodiments, a passive RFID tag (e.g., an RFID tag that does not require a power source but is instead powered by a carrier field provided by another device) can be used to determine test results. For example, in some embodiments, the antenna of an RFID tag can be functionalized such that it is sensitive to a chemical, antibody, and so forth, which can cause the response of the tag to exposure to a carrier field (e.g., as provided by a smartphone or other RFID reader) to change depending upon the test result. Thus, a computer system can be used to readily obtain a result, but there may not be a visible test result that is readable by a human. In some embodiments, an active RFID tag can be used and can be functionalized to modify response based on a test result. In some embodiments, a hybrid tag can be used. The hybrid tag may ordinarily operate in a passive mode but may switch to an active mode in response to the presence of a chemical, antibody, or other material being detected, for example by a chemical reaction that completes or modifies a circuit.

Figure 21:
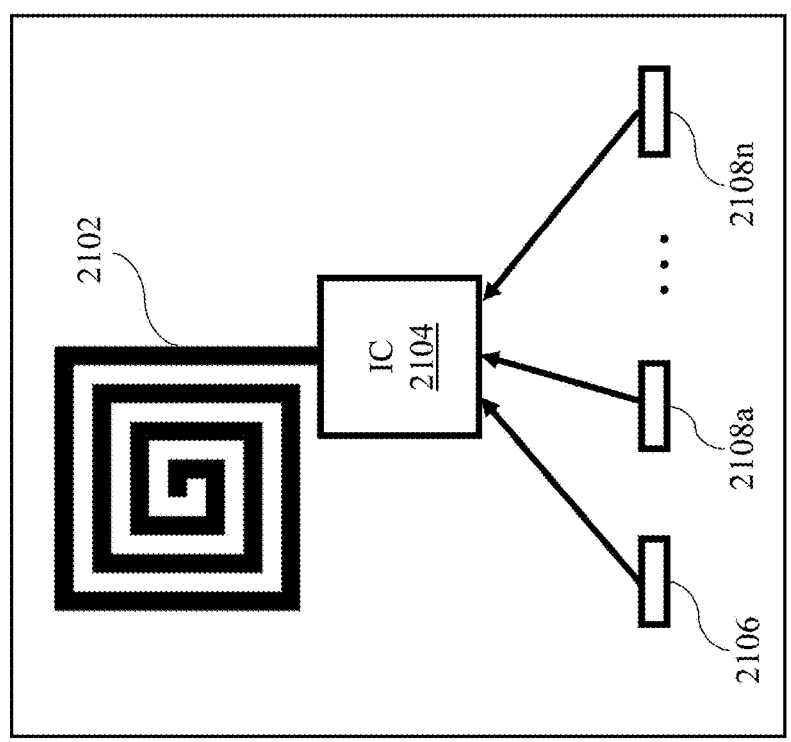
FIGS. 21 and 22 illustrate example RFID or NFC test cards according to some embodiments.

FIG. 21 illustrates an example RFID or NFC system according to some embodiments. The system includes an antenna 2102 in electrical communication with an integrated circuit 2104. A control sensor 2106 is electrically connected to the integrated circuit 2104. One or more biological test sensors 2108a-2108n are in electrical communication with the integrated circuit 2104. In some embodiments, a testing procedure can include inserting a sample, scanning the test card with an NFC reader, waiting a period of time, and scanning again. In some embodiments, start time, user ID information, and so forth can be written to the memory of the integrated circuit 2104 if test starting conditions are met. If end result conditions are met, the system can write the results to the memory of the integrated circuit 2104 and can be retrieved by scanning the test with an NFC or RFID reader.

In some embodiments, a test comprises a rigid card made up of two parts that can be broken at a perforation or score line. After a test is completed, the part of the card containing the test sample can be broken away and disposed of properly. The other part of the card, which can contain an integrated circuit and antenna, can be retained as a physical artifact of the test containing the result and other test information (e.g., name of the user, date taken, and so forth). In some embodiments, a security mechanism can be used to ensure that test results are not changed after the card is broken off. For example, a security mechanism can comprise a fuse or other element, or simply an arrangement of electrical connections that prevents writing information once the card is broken off. For example, an electrical connection to one or more pins used for writing to an IC can be broken upon breaking the card.

Figure 22:
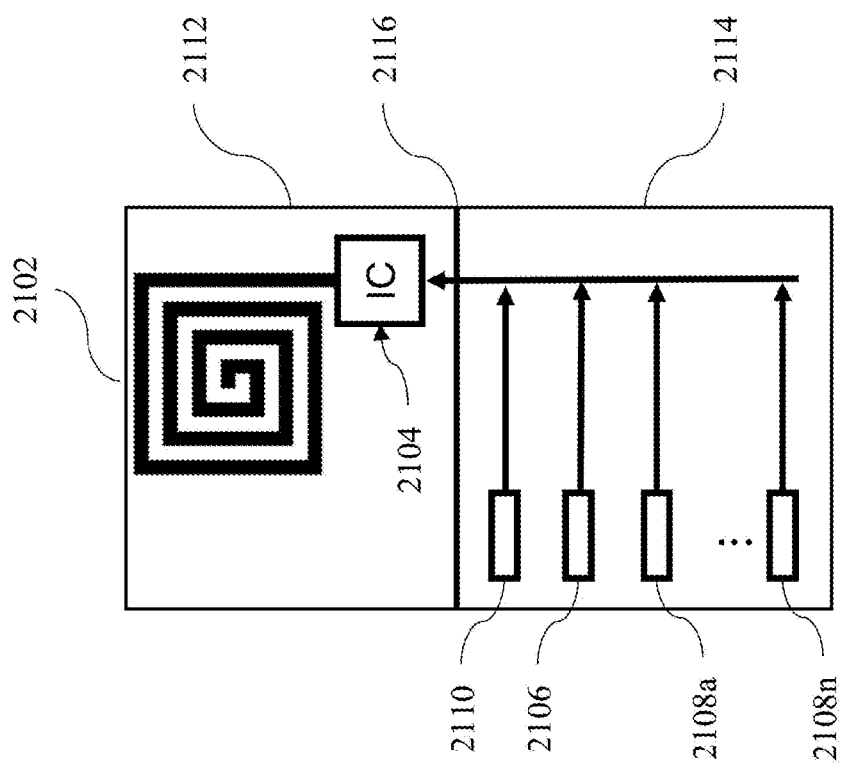

An example embodiment is depicted in FIG. 22. The test card of FIG. 22 is generally similar to that of FIG. 21, except that the test card of FIG. 22 includes a security feature 2110 that prevents writing once the card is broken. The card in FIG. 22 is broken into a result region 2112 and a sampling region 2114, divided by a break line (e.g., a perforation or scored line) 2116 that enables the card to be broken after a test so that a permanent record of test can be retained in the result region 2112 while the sampling region 2114 can be discarded.

As discussed above, an NFC or RFID element can be active (e.g., powered by a battery) or passive. Passive elements can have many advantages, as passive devices are typically simpler and cheaper to produce than active devices that need a battery or another on-board power source. However, passive devices can have significant limitations. For example, a passive device may only be active when it is being read, thus limited its capabilities. In some embodiments, a printable battery can be included on a test card. The printable battery can enable active functionality, such as self-timing, tamper detection, and so forth.

In some embodiments, an integrated circuit may store static information such as a unique ID, manufacturing info such as lot code, test expiration, and so forth. In some embodiments, the integrated circuit can store dynamic information such as, for example, a log of all NFC read times, user information for a test, test dates/times, and/or test results.

In some embodiments, a non-human readable test can be an active device. For example, a non-human readable test can utilize light emitting diodes (LEDs) to present results. For example, in some embodiments, a test may include four LEDs that can be used to communicate with a user. In some embodiments, the LEDs can be used as a progress bar (for example, by lighting one, then two, then three, then four LEDs). For example, when four LEDs are used and the LEDs also serve a progress indicator, eleven states can be used for communicating test results (e.g., of 16 possible LED configurations, 4 are used for progress indication, and the all-off state is excluded because it would appear the same as an inoperable device). Test results can be assigned to binary strings that can be represented by the LEDs, and a computer vision system that knows the relevant key can analyze the LEDs to determine if a test result is negative, positive, or invalid. In some embodiments, the encoding scheme to convert test results into binary values can include salting and/or hashing (e.g., using the serial number of the test) to prevent users from reverse engineering the encoding scheme while a computer system can still easily decode the result. It will be appreciated that four LEDs is merely an example embodiment. In some cases, more or fewer LEDs may be used, or other active elements can be used. For example, instead of a visual code, an active device may provide an audible output that can be detected and decoded by a computer system.

Computer System

Figure 23:
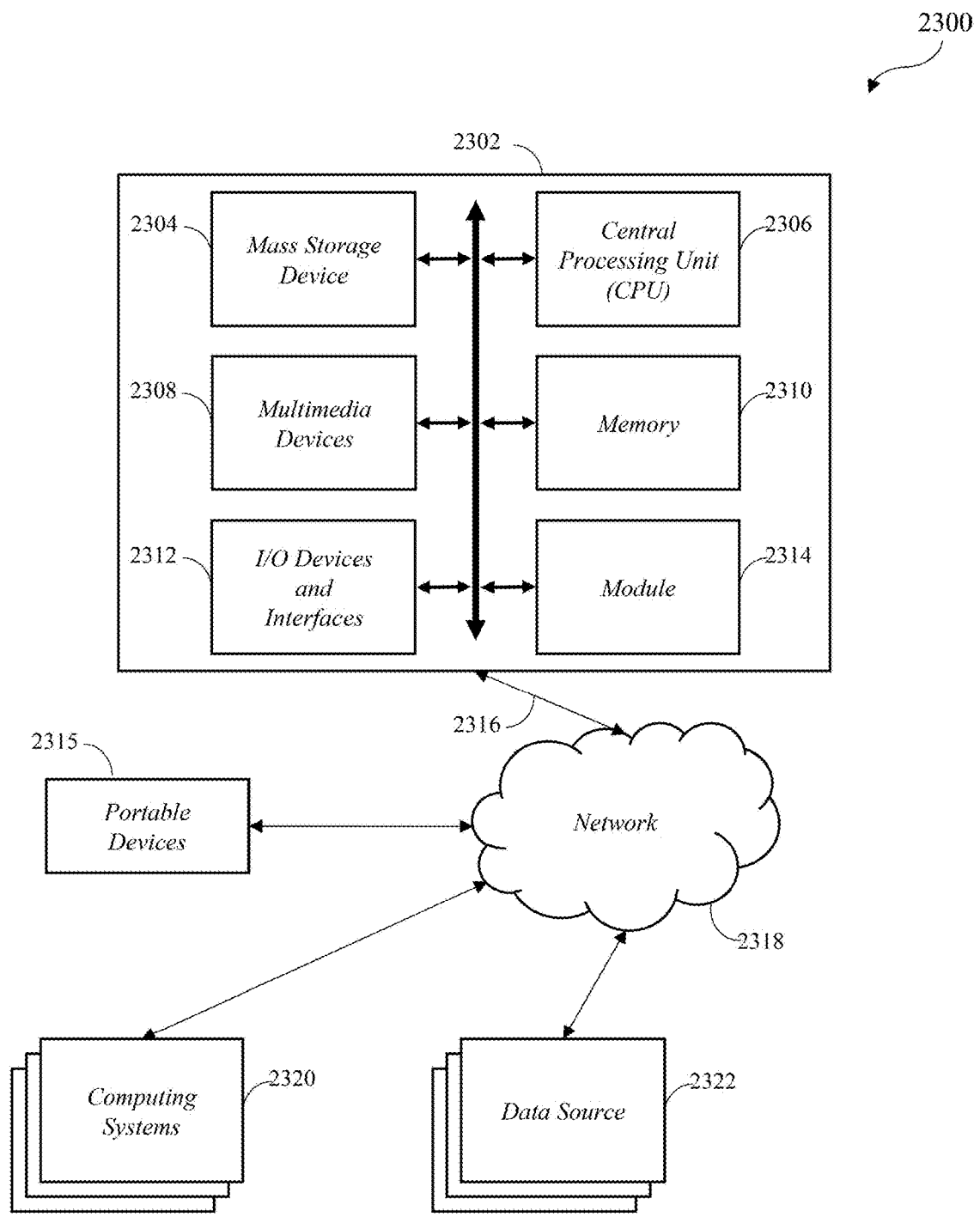
FIG. 23 is a block diagram illustrating an embodiment of a computer hardware system configured to run software for implementing one or more embodiments of the systems and methods described herein.

In some embodiments, the systems, processes, and methods described herein are implemented using a computing system, such as the one illustrated in FIG. 23. The example computer system 2302 is in communication with one or more computing systems 2320, portable devices 2315, and/or one or more data sources 2322 via one or more networks 2318. While FIG. 23 illustrates an embodiment of a computing system 2302, it is recognized that the functionality provided for in the components and modules of computer system 2302 may be combined into fewer components and modules, or further separated into additional components and modules.

The computer system 2302 can comprise a module 2314 that carries out the functions, methods, acts, and/or processes described herein. The module 2314 is executed on the computer system 2302 by a central processing unit 2306 discussed further below.

In general, the word "module," as used herein, refers to logic embodied in hardware or firmware or to a collection of software instructions, having entry and exit points. Modules are written in a programming language, such as Java, C, C++, Python, Ruby, JavaScript, or the like. Software modules may be compiled or linked into an executable program, installed in a dynamic link library, or may be written in an interpreted language such as BASIC, PERL, Lua, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems and may be stored on or within any suitable computer readable medium or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 2302 includes one or more processing units (CPU) 2306, which may comprise a microprocessor. The computer system 2302 further includes a physical memory 2310, such as random access memory (RAM) for temporary storage of information, a read only memory (ROM) for permanent storage of information, and a mass storage device 2304, such as a backing store, hard drive, rotating magnetic disks, solid state disks (SSD), flash memory, phase-change memory (PCM), 3D XPoint memory, diskette, or optical media storage device. Alternatively, the mass storage device may be implemented in an array of servers. Typically, the components of the computer system 2302 are connected to the computer using a standards based bus system. The bus system can be implemented using various protocols, such as Peripheral Component Interconnect (PCI), PCI Express, Micro Channel, SCSI, Industrial Standard Architecture (ISA) and Extended ISA (EISA) architectures.

The computer system 2302 includes one or more input/output (I/O) devices and interfaces 2312, such as a keyboard, mouse, touch pad, and printer. The I/O devices and interfaces 2312 can include one or more display devices, such as a monitor, which allows the visual presentation of data to a user. More particularly, a display device provides for the presentation of GUIs as application software data, and multi-media presentations, for example. The I/O devices and interfaces 2312 can also provide a communications interface to various external devices. The computer system 2302 may comprise one or more multi-media devices 2308, such as speakers, video cards, graphics accelerators, and microphones, for example.

The computer system 2302 may run on a variety of computing devices, such as a server, a Windows server, a Structured Query Language server, a Unix Server, a personal computer, a laptop computer, and so forth. In other embodiments, the computer system 2302 may run on a cluster computer system, a mainframe computer system and/or other computing system suitable for controlling and/or communicating with large databases, performing high volume transaction processing, and generating reports from large databases. The computing system 2302 is generally controlled and coordinated by an operating system software, such as z/OS, Windows, Linux, UNIX, BSD, SunOS, Solaris, macOS, or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 2302 illustrated in FIG. 23 is coupled to a network 2318, such as a LAN, WAN, or the Internet via a communication link 2316 (wired, wireless, or a combination thereof). Network 2318 communicates with various computing devices and/or other electronic devices. Network 2318 is communicating with one or more computing systems 2320 and/or portable devices 2315 and one or more data sources 2322. The module 2314 may access or may be accessed by computing systems 2320, portable devices 2315, and/or data sources 2322 through a web-enabled user access point. Connections may be a direct physical connection, a virtual connection, and other connection type. The web-enabled user access point may comprise a browser module that uses text, graphics, audio, video, and other media to present data and to allow interaction with data via the network 2318.

Access to the module 2314 of the computer system 2302 by computing systems 2320, by portable devices 2315, and/or by data sources 2322 may be through a web-enabled user access point such as the computing systems' 2320 or data source's 2322 personal computer, cellular phone, smartphone, laptop, tablet computer, e-reader device, audio player, or other device capable of connecting to the network 2318. Such a device may have a browser module that is implemented as a module that uses text, graphics, audio, video, and other media to present data and to allow interaction with data via the network 2318.

The output module may be implemented as a combination of an all-points addressable display such as a cathode ray tube (CRT), a liquid crystal display (LCD), a plasma display, or other types and/or combinations of displays. The output module may be implemented to communicate with input devices 2312 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition, a touch screen may act as a hybrid input/output device. In another embodiment, a user may interact with the system more directly such as through a system terminal connected to the score generator without communications over the Internet, a WAN, or LAN, or similar network.

In some embodiments, the system 2302 may comprise a physical or logical connection established between a remote microprocessor and a mainframe host computer for the express purpose of uploading, downloading, or viewing interactive data and databases online in real time. The remote microprocessor may be operated by an entity operating the computer system 2302, including the client server systems or the main server system, and/or may be operated by one or more of the data sources 2322 and/or one or more of the computing systems 2320. In some embodiments, terminal emulation software may be used on the microprocessor for participating in the micro-mainframe link.

In some embodiments, computing systems 2320 who are internal to an entity operating the computer system 2302 may access the module 2314 internally as an application or process run by the CPU 2306.

The computing system 2302 may include one or more internal and/or external data sources (for example, data sources 2322). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 2302 may also access one or more databases 2322. The databases 2322 may be stored in a database or data repository. The computer system 2302 may access the one or more databases 2322 through a network 2318 or may directly access the database or data repository through I/O devices and interfaces 2312. The data repository storing the one or more databases 2322 may reside within the computer system 2302.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

OTHER EMBODIMENT(S)

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present.

What is claimed is:

1. Computer-implemented method of measuring compliance with a medical diagnostic testing procedure comprising:
    providing, by a computing system, a prompt to a user to present a medical diagnostic component to a camera of a user device, wherein the medical diagnostic component is included in a test kit;
    receiving, by the computing system, a first image captured by the camera;
    prompting, by the computing system, the user to present the medical diagnostic component to the camera of the user device;

receiving, by the computing system, a second image captured by the camera;

detecting, by the computing system, a first set of features associated with the first image and a second set of features associated with the second image;

based on the first set of features and the second set of features, determining, by the computing system, that the medical diagnostic component in the first image is the same as the medical diagnostic component in the second image by:

determining, by the computing system, a first plurality of identifiers based on the first set of features, determining, by the computing system, a second plurality of identifiers based on the second set of features, and mapping each identifier of the first plurality of identifiers and the second plurality of identifiers to a hash space comprising hash values, wherein mapping each identifier to a hash space comprises performing a transformation on at least one identifier of the first and second pluralities of identifiers, and wherein the transformation comprises color matching, a scale-invariant feature transform, a convolution transform against a template, thresholding, color matching, edge detection, or overlap detection; and based at least in part on the determining, assessing, by the computing system, that the user remained in compliance with the medical diagnostic testing procedure.

2. The computer-implemented method of claim 1, wherein the medical diagnostic test component is a test strip.

3. The computer-implemented method of claim 2, wherein the test strip includes an identifier comprising one or more of: a QR code, a pattern, a graphic, an image, or a bar code.

4. The method of claim 3, wherein the identifier is unique to a particular test strip.

5. The computer-implemented method of claim 3, wherein the pattern comprises a linear pattern, a color gradient, a grayscale gradient, a sine wave, a triangle wave, a square wave, or an arrangement of shapes.

6. The computer-implemented method of claim 1, wherein the medical diagnostic test component comprises a pattern region.

7. The computer-implemented method of claim 6, wherein the determining comprises:

determining, by the computing system, a first average color value of the first set of features and a second average color value of the second set of features; and comparing the first average color value and the second average color value.

8. The computer-implemented method of claim 1, further comprising:

determining, by the computing system based on the first set of features, a first identifier;

determining, by the computing system based on the second set of features, a second identifier; and determining, by the computing system, that the first identifier is the same as the second identifier.

9. The computer-implemented method of claim 1, wherein the determining comprises:

determining a difference in the hash values of the first plurality of identifiers and the hash values of the second plurality of identifiers.

10. The computer-implemented method of claim 9, wherein the difference in hash values is a Hamming distance or a Levenshtein distance.

11. The computer-implemented method of claim 1, wherein the medical diagnostic test component comprises a reference region.

12. The computer-implemented method of claim 11, wherein the reference region comprises grayscale reference values.

13. The computer-implemented method of claim 11, wherein the reference region comprises color reference values.

14. The computer-implemented method of claim 1, wherein the medical diagnostic component comprises:

a first region having a first pattern;

a second region having a second pattern; and a third region having a third pattern, wherein the determining comprises comparing the first, second, and third regions of the medical diagnostic component of the first image to the first, second, and third regions of the medical diagnostic component the second image.

15. The computer-implemented method of claim 14, wherein the first pattern has a first frequency, wherein the second pattern has a second frequency that is different from the first frequency, and wherein the third pattern has a third frequency that is different from the first frequency and the second frequency.

16. The computer-implemented method of claim 15, wherein the first frequency is larger than the second frequency and the third frequency, wherein the second frequency is larger than the third frequency, and wherein at least one of the ratio of the first frequency to the second frequency, the ratio of the first frequency to the third frequency, and the ratio of the second frequency to the third frequency is not an integer.

17. The computer-implemented method of claim 16, wherein at least one of the ratios is an irrational number.

* * * * *